(12) United States Patent
Langer et al.

(10) Patent No.: US 7,989,091 B2
(45) Date of Patent: Aug. 2, 2011

(54) SILANES CONTAINING PHENOTHIAZINE-S-OXIDE OR PHENOTHIAZINE-S,S-DIOXIDE GROUPS AND THE USE THEREOF IN OLEDS

(75) Inventors: Nicolle Langer, Heppenheim (DE); Klaus Kahle, Ludwigshafen (DE); Christian Lennartz, Schifferstadt (DE); Christian Schildknecht, Mannheim (DE); Simon Nord, Karlsruhe (DE); Oliver Molt, Hirschberg (DE); Evelyn Fuchs, Mannheim (DE); Jens Rudolph, Worms (DE); Gerhard Wagenblast, Wachenheim (DE)

(73) Assignee: BASF SE, Ludwigshafen (DE)

( * ) Notice: Subject to any disclaimer, the term of this patent is extended or adjusted under 35 U.S.C. 154(b) by 42 days.

(21) Appl. No.: 12/597,651

(22) PCT Filed: Apr. 21, 2008

(86) PCT No.: PCT/EP2008/054801
§ 371 (c)(1),
(2), (4) Date: Oct. 26, 2009

(87) PCT Pub. No.: WO2008/132085
PCT Pub. Date: Nov. 6, 2008

(65) Prior Publication Data
US 2010/0187980 A1 Jul. 29, 2010

(30) Foreign Application Priority Data
Apr. 26, 2007 (EP) .................................. 07107055

(51) Int. Cl.
*H01L 51/54* (2006.01)
(52) U.S. Cl. ........................ 428/690; 313/504; 544/38
(58) Field of Classification Search .................. 428/690; 313/504; 544/38
See application file for complete search history.

(56) References Cited

U.S. PATENT DOCUMENTS

| 6,194,089 B1 | 2/2001 | Choong et al. |
| 6,307,083 B1 | 10/2001 | Igarashi |
| 2005/0214572 A1* | 9/2005 | Ogasawara et al. ........... 428/690 |
| 2008/0220287 A1 | 9/2008 | Dotz et al. |
| 2009/0054657 A1 | 2/2009 | Molt et al. |
| 2009/0096367 A1 | 4/2009 | Fuchs et al. |

FOREIGN PATENT DOCUMENTS

| EP | 0 774 883 | 5/1997 |
| JP | 2002 308837 | 10/2002 |
| JP | 2005 220088 | 8/2005 |
| WO | 03 017732 | 2/2003 |
| WO | 2004 095598 | 11/2004 |
| WO | 2005 113704 | 12/2005 |

OTHER PUBLICATIONS

U.S. Appl. No. 12/667,765, filed Jan. 5, 2010, Langer et al.
Baldo, M. A. et al., "Very high-efficiency green organic light-emitting devices based on electrophosphorescence", Applied Physics Letters, vol. 75, No. 1, pp. 4-6 (Jul. 5, 1999).
U.S. Appl. No. 12/306,791, filed Dec. 29, 2008, Fuchs et al.
U.S. Appl. No. 12/441,909, filed Mar. 19, 2009, Schildknecht et al.

* cited by examiner

Primary Examiner — D. Lawrence Tarazano
Assistant Examiner — Gregory Clark
(74) Attorney, Agent, or Firm — Oblon, Spivak, McClelland, Maier & Neustadt, L.L.P.

(57) ABSTRACT

Silanes comprising phenothiazine S-oxide or phenothiazine S,S-dioxide groups, organic light-emitting diodes comprising the inventive silanes, a light-emitting layer comprising at least one inventive silane and at least one triplet emitter, a process for preparing the inventive silanes and the use of the inventive silanes in organic light-emitting diodes, preferably as matrix materials and/or blocker materials for triplet emitters.

12 Claims, No Drawings

SILANES CONTAINING PHENOTHIAZINE-S-OXIDE OR PHENOTHIAZINE-S,S-DIOXIDE GROUPS AND THE USE THEREOF IN OLEDS

The present invention relates to silanes comprising phenothiazine S-oxide or phenothiazine S,S-dioxide groups, to organic light-emitting diodes comprising the inventive silanes, to a light-emitting layer comprising at least one inventive silane and at least one triplet emitter, to a blocker layer comprising at least one inventive silane, to processes for preparing the inventive silanes and to the use of the inventive silanes in organic light-emitting diodes, preferably as matrix materials and/or as blocker materials for triplet emitters.

Organic light-emitting diodes (OLEDs) exploit the property of materials of emitting light when they are excited by electrical current. OLEDs are of particular interest as an alternative to cathode ray tubes and liquid-crystal displays for producing flat visual display units. Owing to the very compact design and the intrinsically low power consumption, devices comprising OLEDs are suitable especially for mobile applications, for example for applications in cell phones, laptops, etc., and for illumination.

The basic principles of the way in which OLEDs function and suitable structures (layers) of OLEDs are known to those skilled in the art and are specified, for example, in WO 2005/113704 and the literature cited therein. The light-emitting materials (emitters) used may, as well as fluorescent materials (fluorescent emitters), be phosphorescent materials (phosphorescence emitters). The phosphorescence emitters are typically organometallic complexes which, in contrast to the fluorescence emitters which exhibit singlet emission, exhibit triplet emission (triplet emitters) (M. A. Baldow et al., Appl. Phys. Lett. 1999. 75, 4 to 6). For quantum-mechanical reasons, when the triplet emitters (phosphorescence emitters) are used, up to four times the quantum efficiency, energy efficiency and power efficiency are possible. In order to implement the advantages of the use of the organometallic triplet emitters (phosphorescence emitters) in practice, it is necessary to provide device compositions which have a high operative lifetime, a high stability against thermal stress and a low use and operating voltage.

Such device compositions may, for example, comprise matrix materials in which the actual light emitters are present in distributed form. In addition, the device compositions may comprise blocker materials, and hole blockers, exciton blockers and/or electron blockers may be present in the device compositions. The selection of the matrix material and of the blocker material used has a significant influence, inter alia, on the luminances and quantum yields of the OLEDs.

The prior art proposes numerous different materials for use in OLEDs. Among the materials proposed are also those which comprise substituted, especially aryl-substituted, silanes.

For instance, US 2005/0214 572 A1 relates to OLEDs which comprise, preferably as the matrix material in the luminescent layer, at least one arylsilane. The arylsilane has at least two aryl radicals which are substituted by a nitrogen-containing heterocycle. The use of arylsilanes which have phenothiazine S-oxide or phenothiazine S,S-dioxide substituents is not disclosed in US 2005/0214 572 A1.

WO 2004/095 598 A2 relates to OLEDs whose light-emitting layer comprises matrix materials which have a large energy gap of at least 3.2 eV. The matrix materials mentioned in WO 2004/095 598 A2 include arylsilanes. The use of phenothiazine S-oxide- or phenothiazine S,S-dioxide-substituted arylsilanes as matrix materials and/or blocker materials is, however, not mentioned in WO 2004/095 598 A2.

JP 2005/22 00 88 A2 relates to arylsilanes whose aryl radicals bear nitrogen-comprising substituents. The compounds according to JP 2005/22 00 88 A2 have an energy gap which is greater than 3.0 eV. According to JP 2005/22 00 88 A2 the arylsilanes mentioned are used as hole transport materials in OLEDs. Use as matrix materials and/or in OLEDs is not mentioned in JP 2005/22 00 88 A2. Furthermore, JP 2005/22 00 88 A2 does not disclose arylsilanes whose aryl radicals bear phenothiazine S-oxide or phenothiazine S,S-dioxide substituents.

JP 2002/30 88 37 A2 relates to compounds which have hole transport properties. According to JP 2002/30 88 37 A2, these compounds may be arylsilanes whose aryl groups are substituted by nitrogen heterocycles. Substitution of the aryl groups by phenothiazine S-oxide or phenothiazine S,S-dioxide substituents is not mentioned in JP 2002/30 88 37 A2. Furthermore, the compounds according to JP 2002/30 88 37 A2 are used as hole transport materials. The use of the compounds as matrix materials in the light-emitting layer and/or blocker materials is not mentioned in JP 2002/30 88 37 A2.

WO 03/017732 A1 relates to OLEDs which comprise a polymerizable amorphous matrix in which a light-emitting material is present. The base structure which forms the polymerizable matrix comprises arylsilane units whose aryl radicals may be substituted, inter alia, by heteroaryl groups. Substitution of the aryl radicals by phenothiazine S-oxide or phenothiazine S,S-dioxide groups is not mentioned in WO 03/017732 A1. Furthermore, the matrix according to WO 03/017732 A1 is a polymerizable amorphous matrix.

U.S. Pat. No. 6,194,089 B1 discloses an OLED which has an organic light-emitting layer which comprises a continuous organic medium $A_xB_yC_z$. In this medium, A is an electron-transporting material, B is a hole-transporting material and C is a hole-injecting material. The materials A, B and C may be present in the continuous organic medium in various concentration gradients within the medium. Component B may, among other compounds, be an arylsilane whose aryl groups may be substituted by aromatic tertiary amino groups. Arylsilanes whose aryl groups are substituted by phenothiazine S-oxide or phenothiazine S,S-dioxide substituents are not mentioned in U.S. Pat. No. 6,194,089 B1.

EP 0 774 883 A2 discloses OLEDs which have a hole transport layer which comprises 2 or more hole transport materials in a mixture. The hole transport materials used may be arylsilanes, and the aryl groups may be substituted by tertiary amine units. With regard to the use of arylsilanes whose aryl groups are substituted by phenothiazine S-oxide or phenothiazine S,S-dioxide units, EP 0 774 883 A2 does not give any information. Furthermore, the arylsilanes according to EP 0 774 883 A2 are used in the hole-transporting layer as hole transport materials and not as matrix materials in the light-emitting layer and/or as blocker materials.

It is therefore an object of the present application with respect to the prior art to provide novel matrix materials and novel blocker materials for use in OLEDs, especially in the light-emitting layers of the OLEDs, which preferably serve as matrix materials and/or blocker materials for triplet emitters. The materials should be easily obtainable and, in combination with the emitter(s), bring about good luminances and quantum yields in OLEDs.

This object is achieved by the provision of compounds of the general formula I

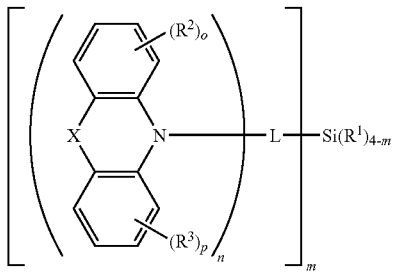

in which

X is SO$_2$ or SO, preferably SO$_2$;

R$^1$ is in each case independently optionally substituted aryl, optionally substituted heteroaryl or optionally substituted alkyl;

R$^2$, R$^3$ are in each case independently optionally substituted alkyl, optionally substituted aryl, optionally substituted heteroaryl or substituents having donor or acceptor action, such as alkoxy, aryloxy, arylcarbonyloxy (—C=O(OR)), —C=O(SR), heteroaryl, hydroxyl, amino, halogen, —C=O(R), —OC=O(R), —SC=O(R), amido (—C=O(NR)), —NRC=O(R), sulfonyl, sulfonamide, vinyl, CN, nitro, thioalkoxy, thioaryloxy or SiR$_3$, where R is in each case independently hydrogen, alkyl or aryl;

m is 1, 2, 3 or 4, preferably 2, 3 or 4;

n is 1 or 2;

o, p are each independently 0, 1, 2, 3 or 4, preferably 0, 1 or 2, more preferably 0;

L is a bridging group selected from the group consisting of

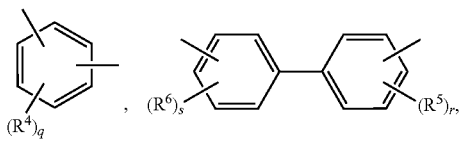

—CH$_2$—(B)$_j$— and optionally substituted heteroarylene;

R$^4$, R$^5$, R$^6$ are in each case independently optionally substituted alkyl, optionally substituted aryl, optionally substituted heteroaryl or substituents having donor or acceptor action; such as alkoxy, aryloxy, arylcarbonyloxy (—C=O(OR)), —C=O(SR), heteroaryl, hydroxyl, amino, halogen, —C=O(R), —OC=O(R), —SC=O(R), amido (—C=O(NR)), —NRC=O(R), sulfonyl, sulfonamide, vinyl, CN, nitro, thioalkoxy, thioaryloxy or SiR$_3$, where R is in each case independently hydrogen, alkyl or aryl;

q, r, s are each independently 0, 1, 2, 3 or 4, preferably 0, 1 or 2, more preferably 0;

B is an alkylene group —C$_k$H$_{2k}$—CH$_2$—, in which one or more nonadjacent CH$_2$ groups of the —C$_k$H$_{2k}$— unit may be replaced by oxygen or NR$^7$;

R$^7$ is aryl or alkyl;

k is 1, 2, 3, 4, 5, 6, 7 or 8; and j is 0 or 1.

The inventive compounds of the formula I are suitable especially as matrix materials and/or blocker materials for use in OLEDs. They are preferably used as matrix materials in the light-emitting layer together with the actual emitter. The emitter which is used together with the matrix materials in the light-emitting layer of an OLED is more preferably a triplet emitter. In a further embodiment, the compounds of the formula (I) are used as hole/photon-exciton blockers.

The compounds of the formula I are readily obtainable and have, both when used as matrix materials and when used as blocker materials in combination with the actual emitter(s), good luminances and quantum yields when used in OLEDs.

Depending on their substitution pattern, the compounds of the formula (I) may be used either as an electron-conducting matrix and/or hole/exciton blocker or as a hole-conducting or ambipolar matrix and/or electron/exciton blocker.

Electron-conducting Matrix and/or Hole/Exciton Blocker

Compounds of the formula I which do not have any electron-donating substituents R$^2$, R$^3$, R$^4$, R$^5$, R$^6$ (i.e. substituents with +I and/or +M effect) can essentially only conduct electrons and are therefore generally used as an electron-conducting matrix and/or hole/exciton blocker.

Ambipolar Matrix and/or Either Hole/Exciton Blocker or Electron/Exciton Blocker

Compounds of the formula I which have electron-donating substituents R$^2$, R$^3$, R$^4$, R$^5$, R$^6$ can conduct either electrons or holes. They can therefore be used as an electron- and hole-conducting matrix (ambipolar matrix). Depending on the system (OLED construction), they can be used as a hole/exciton blocker or as an electron/exciton blocker. In general, the more electron-donating substituents are present in the compounds of the formula I, the better the suitability of the compounds of the formula I as a hole-conducting matrix and/or electron/exciton blocker.

The expressions electron-donating substituents (+I and/or +M effect) and electron-withdrawing substituents (–I and/or –M effect) are used in the present application in the customary sense known to those skilled in the art. Suitable electron-donating and electron-withdrawing substituents are, for example, amino groups, alkoxy groups, halogen substituents, aryloxy groups, arylcarbonyloxy groups, heteroaryl groups, hydroxyl groups, —C=O(R), —OC=O(R), —SC=O(R), amido groups, —NRC=O(R), sulfone groups, sulfonamide groups, vinyl groups, CN, nitro groups, thioalkoxy groups, thioaryloxy groups or SiR$_3$, where R is in each case hydrogen, alkyl or aryl, or halogenated alkyl groups, e.g. CF$_3$.

Preference is given to using the compounds of the formula (I) as an electron-conducting matrix and/or hole-exciton blocker. This means that, in a preferred embodiment, the present invention relates to compounds of the formula (I) which do not have any electron-donating substituents R$^2$, R$^3$, R$^4$, R$^5$, R$^6$.

The alkyl radicals, and also the alkyl radicals of the alkoxy groups, according to the present application, may be either straight-chain or branched, or cyclic and/or optionally substituted by substituents selected from the group consisting of aryl, alkoxy and halogen. Suitable aryl substituents are specified below. Examples of suitable alkyl groups are methyl, ethyl, propyl, butyl, pentyl, hexyl, heptyl and octyl, and also aryl-, alkoxy- and/or halogen-substituted, especially F-substituted, derivatives of the alkyl groups mentioned, such as CF$_3$. Both the n-isomers of these radicals and branched isomers such as isopropyl, isobutyl, isopentyl, sec-butyl, tert-butyl, neopentyl, 3,3-dimethylbutyl, 2-ethylhexyl, etc., are also included. Preferred alkyl groups are methyl, ethyl, tert-butyl and CF$_3$.

The cyclic alkyl radicals, according to the present application, may optionally be substituted by substituents selected from the group consisting of aryl, alkoxy and halogen. The cyclic alkyl radicals are preferably unsubstituted. Suitable aryl substituents are specified below. Examples of suitable cyclic alkyl radicals are cyclopropyl, cyclobutyl, cyclopentyl, cyclohexyl, cycloheptyl, cyclooctyl, cyclononyl and cyclodecyl. If appropriate, the cyclic alkyl radicals may also be polycyclic ring systems, such as decalinyl, norbornanyl, bornanyl or adamantyl. The cyclic alkyl radicals may be unsubstituted or optionally substituted by one or more further radicals, especially alkyl, aryl, alkoxy and/or halogen.

Suitable halogen substituents in the context of the present application are fluorine, chlorine, bromine and iodine, preferably fluorine, chlorine and bromine, more preferably fluorine and chlorine.

Suitable alkoxy and thioalkoxy groups derive correspondingly from the alkyl radicals as have been defined above. Examples here include $OCH_3$, $OC_2H_5$, $OC_3H_7$, $OC_4H_9$ and $OC_8H_{17}$ and also $SCH_3$, $SC_2H_5$, $SC_3H_7$, $SC_4H_9$ and $SC_8H_{17}$. $C_3H_7$, $C_4H_9$ and $C_8H_{17}$ include both the n-isomers and branched isomers such as isopropyl, isobutyl, sec-butyl, tert-butyl and 2-ethylhexyl. Particular preference is given to methoxy, ethoxy, n-octyloxy, 2-ethylhexyloxy and $SCH_3$.

In the present invention, aryl refers to radicals which are derived from monocyclic, bicylic or tricyclic aromatics which do not comprise any ring heteroatoms. When they are not monocyclic systems, the saturated form (perhydro form) or the partly unsaturated form (for example the dihydro form or tetrahydro form), provided that the particular forms are known and stable, are also possible for the term "aryl" for the second ring. This means that the term "aryl" in the present invention, for example, also comprises bicyclic or tricyclic radicals in which either both or all three radicals are aromatic or bicyclic or tricyclic radicals in which only one ring is aromatic, and also tricyclic radicals in which two rings are aromatic. Examples of aryl are: phenyl, naphthyl, indanyl, 1,2-dihydronaphthenyl, 1,4-dihydronaphthenyl, indenyl, anthracenyl, phenanthrenyl or 1,2,3,4-tetrahydronaphthyl. Aryl is more preferably phenyl or napthyl, most preferably phenyl.

The aryl radicals may be unsubstituted or substituted by one or more further radicals. Suitable further radicals are selected from the group consisting of alkyl, aryl or substituents having donor or acceptor action, such as alkoxy, aryloxy, arylcarbonyloxy, heteroaryl, hydroxyl, amino, halogen, —C═O(R), —OC═O(R), —SC═O(R), amido(—C═O(NR)), —NRC═O(R), sulfone, sulfonamide, vinyl, CN, nitro, thioalkoxy, thioaryloxy or $SiR_3$, where R is in each case independently hydrogen, alkyl or aryl. The alkyl radicals are preferably unsubstituted or substituted by one or more alkoxy groups, cyano or $CF_3$ or F. Aryl is more preferably unsubstituted phenyl, 4-alkylphenyl, 4-alkoxyphenyl, 2,4,6-trialkylphenyl, 2,4,6-trialkoxyphenyl or N,N-diarylaminophenyl, preferably 4-methylphenyl, 4-methoxyphenyl, 2,4,6-trimethylphenyl, 2,4,6-trimethoxyphenyl, 9-phenylcarbazolyl, and the corresponding benzofused radicals.

Suitable aryloxy, arylthio and arylcarbonyloxy groups derive correspondingly from the aryl radicals as have been defined above. Particular preference is given to phenoxy, phenylthio and phenylcarbonyloxy.

Suitable amino groups have the general formula —NR'R" where R' and R" are each independently alkyl or aryl. Suitable alkyl and aryl radicals, each of which may optionally be substituted, have been specified above. Examples of suitable amino groups are diarylamino groups such as diphenylamino, and dialkylamino groups such as dimethylamino, diethylamino, arylalkylamino such as phenylmethylamino.

Heteroaryl is understood to mean monocyclic, bicyclic or tricyclic heteroaromatics which can be derived partly from the aforementioned aryl by replacing at least one carbon atom in the aryl base skeleton with a heteroatom. Preferred heteroatoms are N, O and S. The base skeleton is especially preferably selected from systems such as pyridine and five-membered heteroaromatics such as thiophene, pyrrole, imidazole or furan. These base skeletons may optionally be fused to one or two 6-membered aromatic radicals. Suitable systems are carbazolyl, benzimidazolyl, benzofuryl, dibenzofuryl or dibenzothiophenyl. The base skeleton may be substituted at one, more than one or all substitutable positions, in which case suitable substituents are the same as have already been specified under the definition of aryl. However, the heteroaryl radicals are preferably unsubstituted. Particular mention should be made here of pyridin-2-yl, pyridin-3-yl, pyridin-4-yl, thiophen-2-yl, thiophen-3-yl, pyrrol-2-yl, pyrrol-3-yl, furan-2-yl, furan-3-yl and imidazol-2-yl, and the corresponding benzofused radicals, especially benzimidazolyl, benzofuryl, dibenzofuryl or dibenzothiophenyl.

Heterocyclic alkyl is understood to mean radicals which differ from the aforementioned cyclic alkyl in that at least one carbon atom has been replaced by a heteroatom in the cyclic alkyl base skeleton. Preferred heteroatoms are N, O and S. The base skeleton may be substituted at one, more than one or all substitutable positions, in which case suitable substituents are the same as have already been specified under the definition of aryl. Particular mention should be made here of the nitrogen-containing radicals pyrrolidin-2-yl, pyrrolidin-3-yl, piperidin-2-yl, piperidin-3-yl, piperidin-4-yl.

Groups having donor or acceptor action in the context of the present application are understood to mean the following groups:

Groups having donor action are understood to mean groups which have a +I and/or +M effect, and groups having acceptor action are understood to mean groups which have a −I and/or −M effect. Suitable groups having donor or acceptor action are halogen radicals, preferably F, Cl, Br, I, more preferably F, Cl, halogenated alkyl radicals, e.g. $CF_3$, alkoxy radicals, aryloxy radicals, carbonyl radicals, ester radicals, both oxycarbonyl and carbonyloxy, e.g. arylcarbonyloxy, amine radicals, amide radicals, —NR(═OCR), $CH_2F$ groups, $CF_3$ groups, CN groups, thio groups, thioalkoxy groups, thioaryloxy groups, sulfonic acid groups, thiocarbonyl, carbonylthio, sulfonic ester groups, boronic acid groups, boronic ester groups, phosphonic acid groups, phosphonic ester groups, phosphine radicals, sulfoxide radicals, sulfonyl radicals, sulfonamide groups, sulfide radicals, nitro groups, OCN, boran radicals, silyl groups, stannate radicals, imino groups, hydrazine radicals, hydrazole radicals, oxime radicals, nitroso groups, diazo groups, $SiR_3$ groups, phosphine oxide groups, hydroxyl groups, vinyl groups, heteroaryl groups or SCN groups. Preferred groups having donor or acceptor action are alkoxy, aryloxy, arylcarbonyloxy ((—C═O(OR)), carbonylthio (—C═O(SR), heteroaryl, hydroxyl, amino, halogen, carbonyl (—C═O(R)), oxycarbonyl (—OC═O(R)), thiocarbonyl (—SC═O(R)), amido (—C═O(NR)), —NRC═O(R), sulfonyl, sulfonamide groups, vinyl, thioalkoxy, thioaryloxy or $SiR_3$, where R is in each case independently hydrogen, alkyl or aryl. Very particular preference is given to F, Cl, CN, aryloxy, alkoxy and halogenated alkyl radicals, e.g. $CF_3$.

A sulfonamide radical is understood to mean —$SO_2$NHR in which R is hydrogen, alkyl or aryl, preferably hydrogen, $C_1$-$C_6$-alkyl, phenyl or benzyl.

Sulfonyl is understood to mean —$S(O)_2$R in which R is hydrogen, alkyl, aryl or amino, preferably hydrogen, $C_1$-$C_6$-alkyl, phenyl, benzyl or —NR'$_2$, in which R' is in each case independently oxygen, alkyl or aryl, preferably hydrogen, $C_1$-$C_6$-alkyl or benzyl.

The —$C_kH_{2k}$— unit of the alkylene bridge B is understood to mean especially the linear alkylene chains —$CH_2$—, —$(CH_2)_2$—, —$(CH_2)_3$—, —$(CH_2)_4$—, —$(CH_2)_5$—, —$(CH_2)_6$—, —$(CH_2)_7$— and —$(CH_2)_8$—. However, they may also be branched, such that, for example, —$CH(CH_3)$—, —$C(CH_3)_2$—, —$CH_2$—$CH(CH_3)$—, —$CH(CH_3)$—$CH(CH_3)$—, —$C(CH_3)_2$—$C(CH_3)_2$—, —$CH(CH_3)$—$CH_2$—$CH(CH_3)$—, —$CH(CH_3)$—$(CH_2)_2$—$CH(CH_3)$—, —$CH(CH_3)$—$(CH_2)_3$—$CH(CH_3)$—, —$CH(CH_3)$—$(CH_2)_4$—$CH(CH_3)$—, —$C(CH_3)_2$—$CH_2$—$C(CH_3)_2$— or —$C(CH_3)_2$—$(CH_2)_2$—$C(CH_3)_2$— chains are also possible. Furthermore, in the —$C_kH_{2k}$— unit of the alkylene bridge B, one or more nonadjacent $CH_2$ groups may be replaced by hydrogen or NR. Examples thereof are especially —O—$C_2H_4$—O—, —O—$(C_2H_4$—O—$)_2$, —NR—$C_2H_4$—NR—, or —NR—$(C_2H_4$—NR—$)_2$, where R is especially alkyl such as methyl, ethyl, propyl, isopropyl, butyl, sec-butyl or tert-butyl, or aryl such as phenyl.

$R^1$ in the compounds of the formula I is in each case independently selected from the group consisting of optionally substituted aryl, optionally substituted heteroaryl and optionally substituted alkyl, suitable aryl, heteroaryl and alkyl groups and suitable substituents already having been specified above. $R^1$ is preferably alkyl, especially methyl, ethyl or propyl, more preferably methyl, or unsubstituted or substituted aryl, preferably unsubstituted or substituted phenyl, in which case the substituents on the phenyl are alkyl which is preferably substituted by halogen, alkoxy, CN or an amino substituent, e.g. $CF_3$, $OCH_3$, CN or diarylamino. The aryl radical is preferably substituted by from 1 to 3 amino substituents, more preferably by diarylamino substituents, especially by diphenylamino substituents; heteroaryl, preferably N-carbazolyl and derivatives thereof. The $R^1$ radicals are most preferably each independently phenyl, methyl, 9-phenylcarbazolyl or 4-N,N-diphenylaminophenyl.

The compounds of the formula I comprise 0, 1, 2 or up to 3 $R^1$ radicals. This means that m in the compounds of the formula I may be 1, 2, 3 or 4; m is preferably 2, 3 or 4. In the case when m is 4, the compound of the formula I does not comprise any $R^1$ radicals.

$R^2$ and $R^3$ in formula I are each independently optionally substituted alkyl, optionally substituted aryl or optionally substituted heteroaryl, suitable alkyl, aryl and heteroaryl groups and suitable substituents having been specified above, or substituents with donor or acceptor action. Suitable substituents with donor or acceptor action are specified above. Preferred substituents with donor or acceptor action are: halogenated alkyl radicals, e.g. $CF_3$, alkoxy, aryloxy, arylcarbonyloxy (—C═O(OR)), —C═O(SR), heteroaryl, hydroxyl, amino, halogen, —C═O(R), —OC═O(R), —SC═O(R), amido (—C═O(NR)), —NRC═O(R), sulfonyl, sulfonamide, vinyl, CN, nitro, thioalkoxy, thioaryloxy or $SiR_3$, where R is in each case independently hydrogen, alkyl or aryl.

o and p in formula I are each independently 0, 1, 2, 3 or 4, preferably 0, 1 or 2, more preferably 0. In the case when o or p is 0, respectively, no $R^2$ or $R^3$ radicals are present in the compounds of the formula I, i.e. all substitutable positions of the phenothiazine S-oxide or phenothiazine S,S-dioxide radical are substituted by hydrogen atoms.

The bridging L group is a group selected from the group consisting of

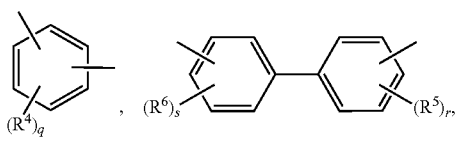

—$CH_2$—$(B)_j$— and optionally substituted heteroarylene, where the $R^4$, $R^5$ and $R^6$ radicals are in each case independently optionally substituted alkyl, optionally substituted aryl, optionally substituted heteroaryl or substituents having donor or acceptor action. Suitable alkyl, aryl, heteroaryl groups and groups having donor or acceptor action have already been specified above.

q, r, s may each independently be 0, 1, 2, 3 or 4, preferably 0, 1 or 2, more preferably 0. In the case in which q, r or s is 0, the bridging L groups, respectively, do not comprise any substituents $R^4$, $R^5$ or $R^6$, i.e. all substitutable positions of the bridging L groups bear hydrogen atoms.

In the case that the bridging L group is a —$CH_2$—$(B)_j$- group, B is an alkylene group —$C_kH_{2k}$—$CH_2$— in which one or more nonadjacent $CH_2$ groups of the —$C_kH_{2k}$-unit may be replaced by oxygen or $NR^7$.

$R^7$ is an aryl or alkyl, suitable alkyl groups already having been specified above. Particularly preferred alkyl groups are methyl and ethyl. Aryl is preferably phenyl.

k in the alkylene group B may be 1, 2, 3, 4, 5, 6, 7 or 8. j is 0 or 1.

In a preferred embodiment, the B group is an alkylene group in which none of the —$C_kH_{2k}$-units are replaced by oxygen or $NR^7$. The alkylene groups are thus preferably alkylene groups of the general formula —$(CH_2)_{1-9}$—. The bridging L group may thus be an alkylene group which is formed from 1 to 10 $CH_2$ groups.

Optionally substituted heteroarylene groups used with preference as the L group have one of the following formulae:

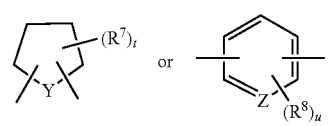

where
$R^7$ and $R^8$ are each independently optionally substituted alkyl, optionally substituted heteroaryl or substituents having donor or acceptor action, suitable alkyl, aryl, heteroaryl groups and groups having donor or acceptor action already having been specified above; and
Y is NR', PR', S, O, where R' is alkyl or aryl and suitable alkyl and aryl groups are specified above;
Z is N
t is 0, 1 or 2; and
u is 0, 1, 2 or 3,
where, in the case when t or u is 0, all substitutable positions bear hydrogen atoms.

In a preferred embodiment, the L group is a bridging group selected from the group consisting of

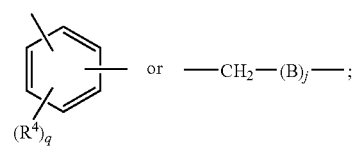

more preferably, the bridging L group is

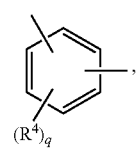

most preferably

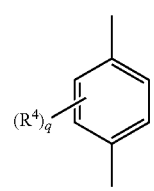

The $R^4$, $R^5$ and $R^6$ radicals and the indices q, j are each as defined above. In a particularly preferred embodiment, q, r and s are each 0, i.e. the substitutable positions of the aforementioned bridging L groups bear hydrogen atoms.

The present invention preferably relates to compounds of the formula I in which:
X is $SO_2$;
m is 2, 3 or 4;
o, p are each 0, 1 or 2, preferably 0;

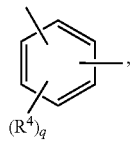 L preferably

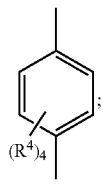

and
q is 0, 1 or 2, preferably 0.

In a further preferred embodiment, the present invention relates to compounds of the formula I in which at least two of the L or $R^1$ radicals or groups bonded to the Si are aromatic radicals or groups.

In a preferred embodiment, the present invention relates to compounds of the formula (I) in which:
$R^2$, $R^3$ are each hydrogen;
o, p are each 0;
n is 1 or 2;
L is 1,4-phenylene or 1,2-ethylene;
m is 1, 2, 3 or 4; and
$R^1$ is the same or different and is $CH_3$, Ph,

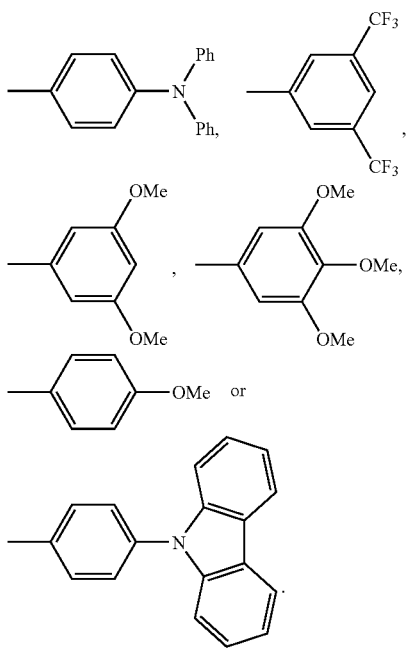

Examples of particularly preferred compounds of the formula I are specified below:

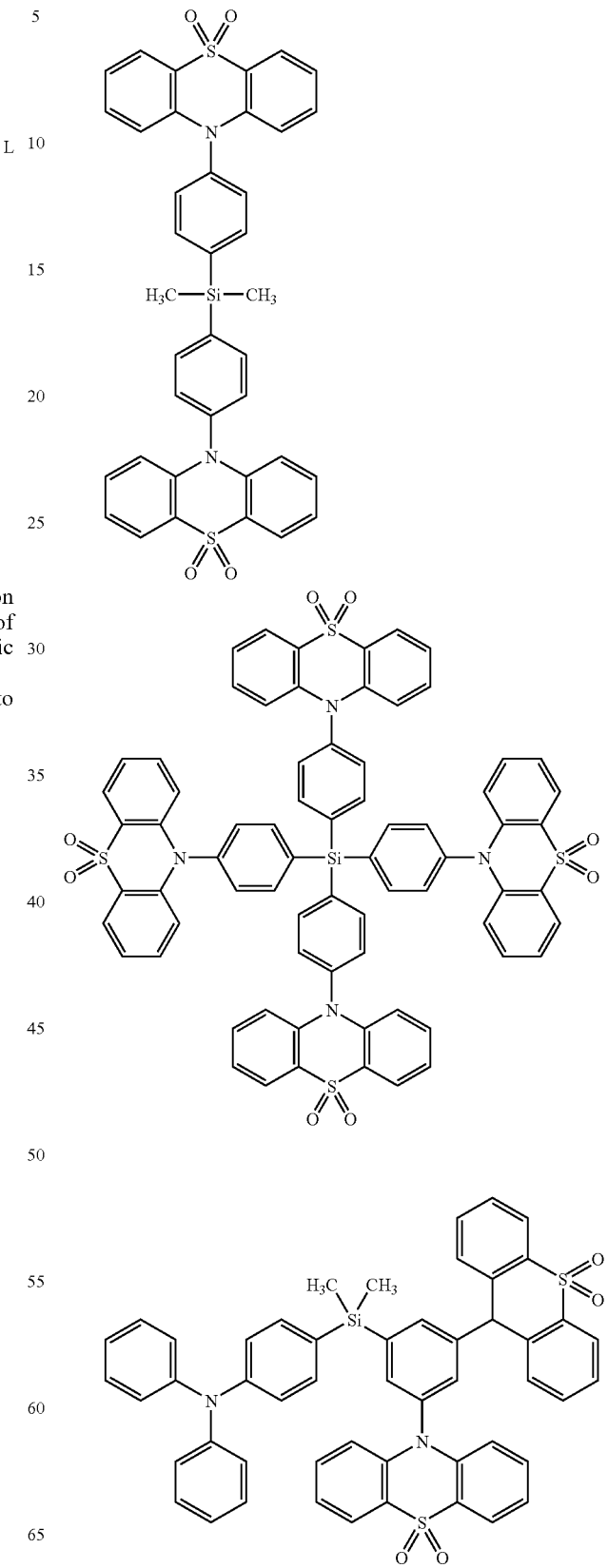

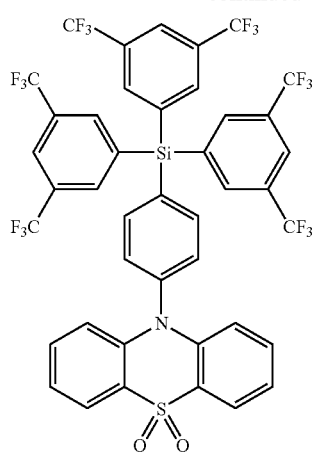
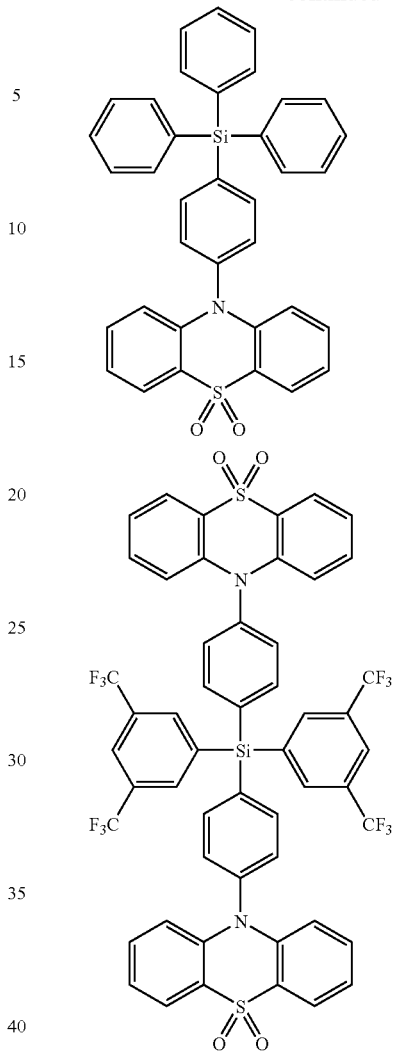
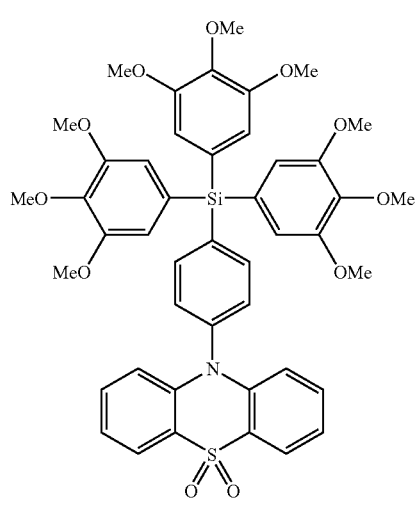
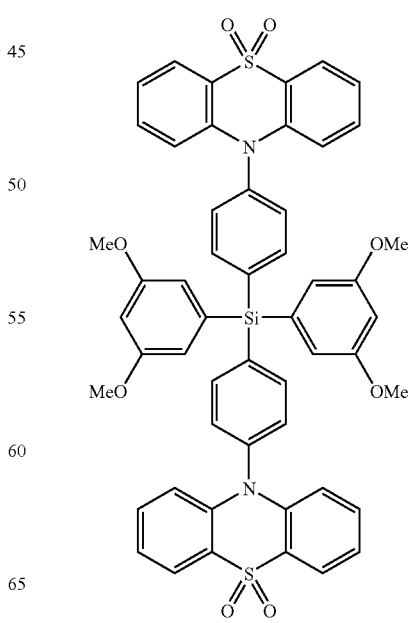

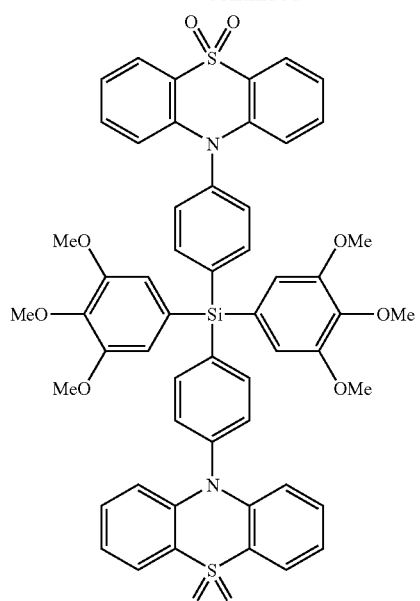
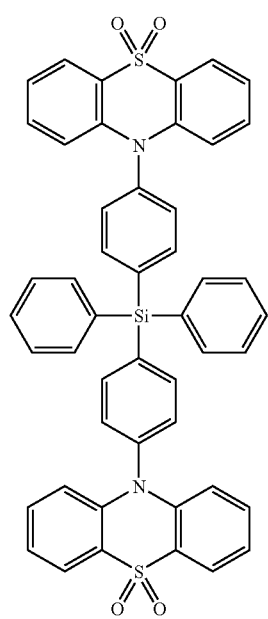
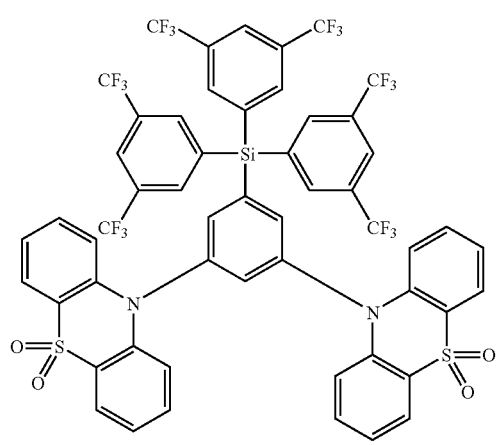
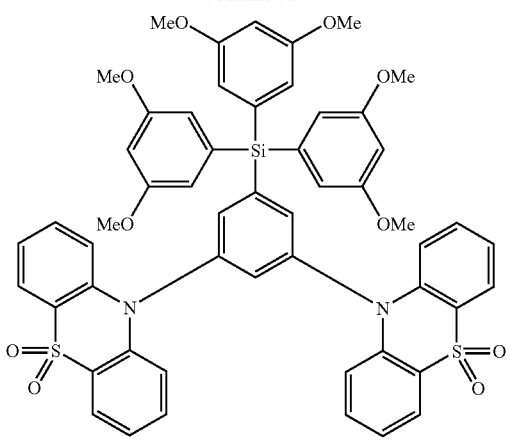
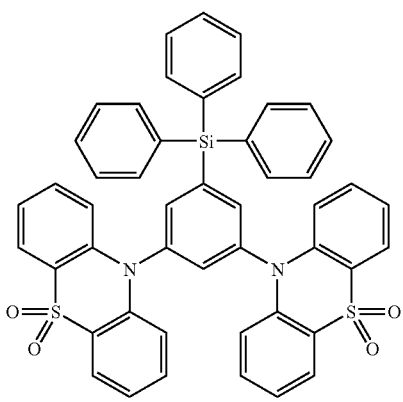
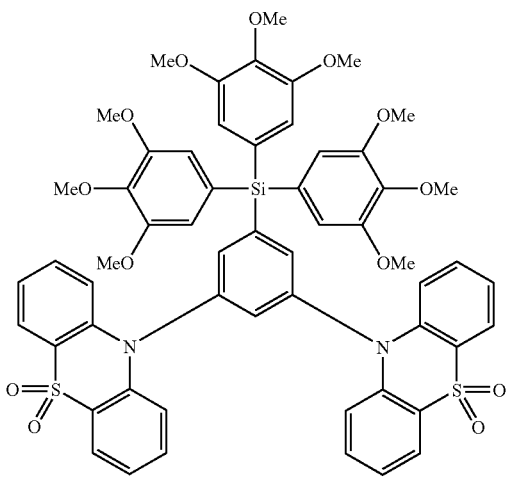

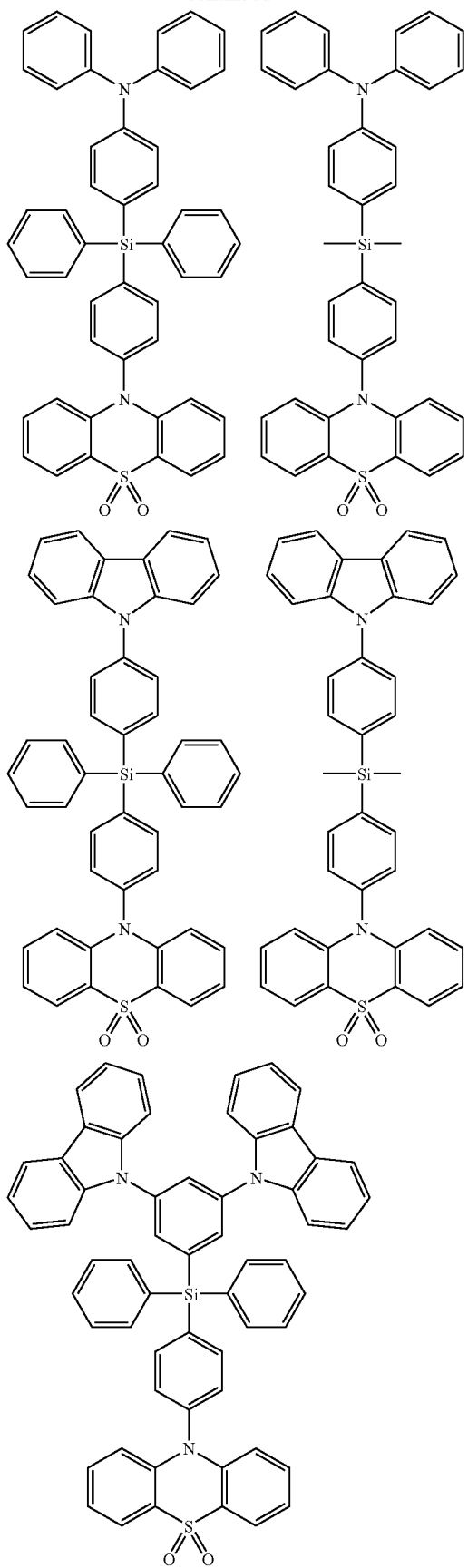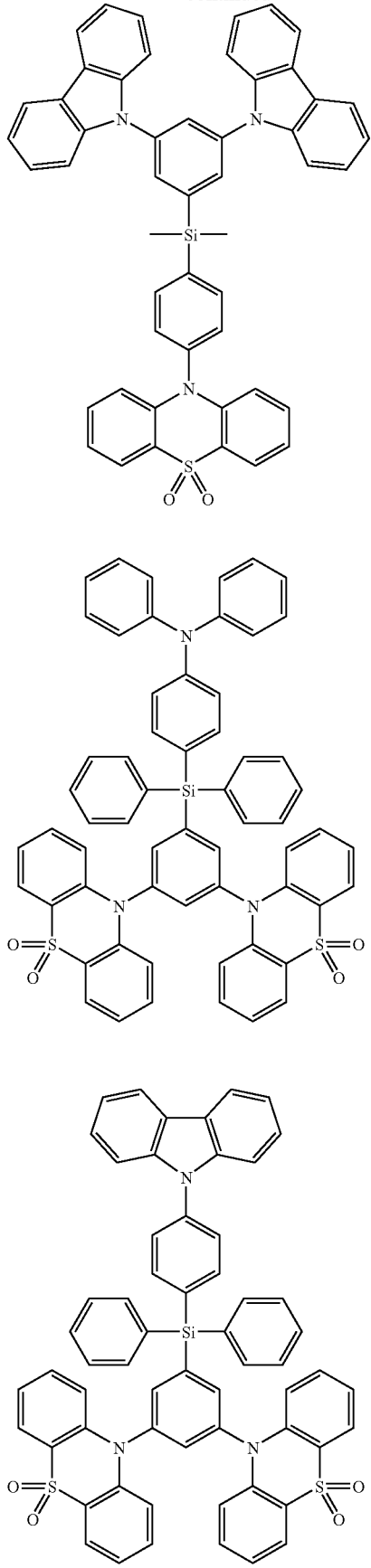

17
-continued
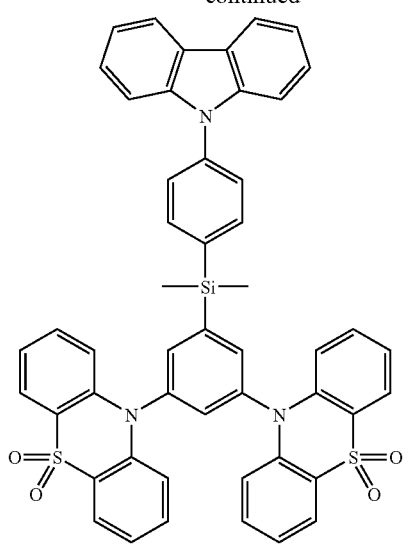
18
-continued
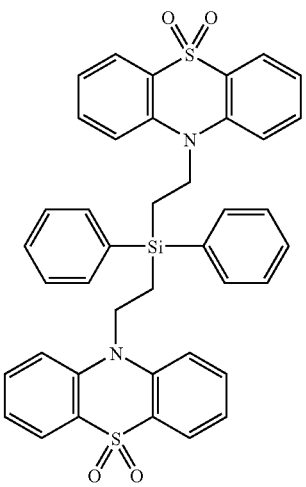
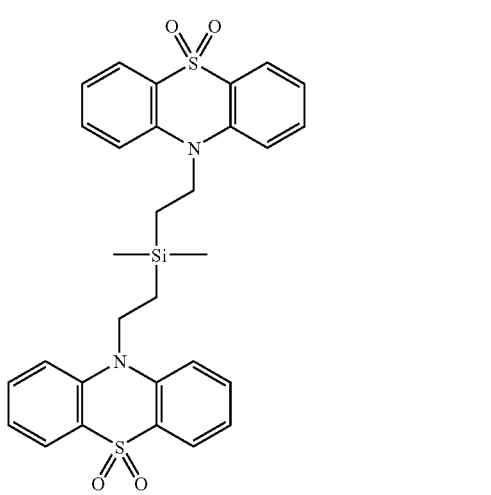
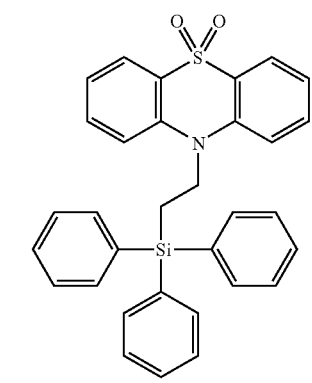
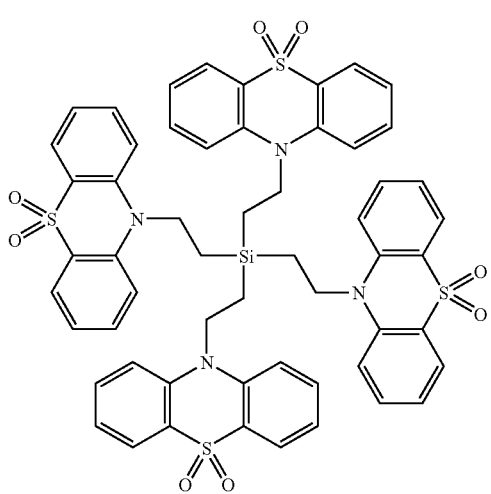
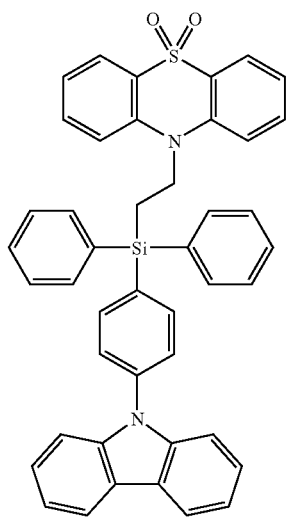

-continued

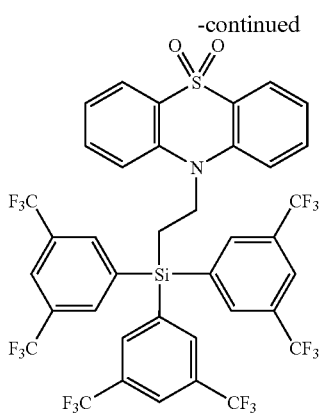

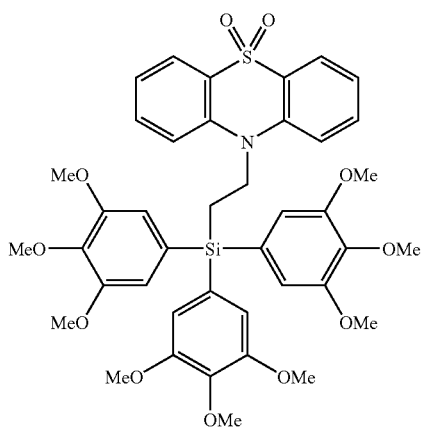

In addition to the compounds mentioned, further variations of the L group and of the indices n and m are possible. For example, the compounds of the formula (I) may additionally have three phenothiazine S,S-dioxide groups and one $R^1$ radical.

The inventive compounds of the formula I can be prepared by all suitable processes known to those skilled in the art. Preference is given to preparing the compounds of the formula I by a process comprising the steps of:
(i) preparing a phenothiazine derivative (II)

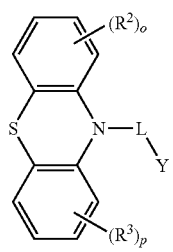
(II)

in which
$R^2$, $R^3$ are in each case independently optionally substituted alkyl, optionally substituted aryl, optionally substituted heteroaryl or a radical having donor or acceptor action; such as alkoxy, aryloxy, arylcarbonyloxy (—C=O(OR)), —C=O(SR), heteroaryl, hydroxyl, amino, halogen, —C=O(R), —OC=O(R), —SC=O(R), amido (—C=O(NR)), —NRC=O(R), sulfonyl, sulfonamide, vinyl, CN, nitro, thioalkoxy, thioaryloxy or $SiR_3$, where R is in each case independently hydrogen, alkyl, aryl or halogenated alkyl;

o, p are each independently 0, 1, 2, 3 or 4, preferably 0, 1 or 2, more preferably 0;

L is a bridging group selected from the group consisting of

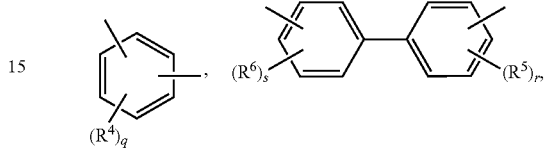

—$CH_2$—(B)$_j$— and optionally substituted heteroarylene;

$R^4$, $R^5$, $R^6$ are in each case independently optionally substituted alkyl, optionally substituted aryl, optionally substituted heteroaryl or a radical having donor or acceptor action; such as alkoxy, aryloxy, arylcarbonyloxy (—C=O (OR)), carbonylthio (—C=O(SR)), heteroaryl, hydroxyl, amino, halogen, carbonyl (C=O(R)), —NRC=O(R), sulfonyl, sulfonamide groups, vinyl, thioalkoxy, thioaryloxy or $SiR_3$, where R is in each case independently hydrogen, alkyl, halogenated alkyl or aryl;

q, r, s are each independently 0, 1, 2, 3 or 4, preferably 0, 1 or 2, more preferably 0;

B is an alkylene bridge —$C_kH_{2k}$—$CH_2$—, in which one or more nonadjacent $CH_2$ groups of the —$C_kH_{2k}$— unit may be replaced by oxygen or $NR^7$;

$R^7$ is hydrogen or alkyl;

k is 1, 2, 3, 4, 5, 6, 7 or 8; and j is 0 or 1; and

Y is halogen, preferably selected from the group consisting of Cl and Br, more preferably Br;

by reacting phenothiazine or a phenothiazine derivative of the formula (III)

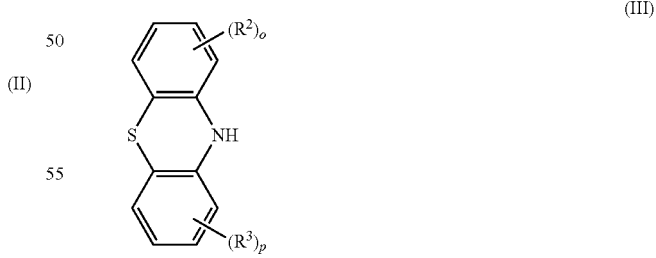

in which $R^2$, $R^3$, o and p are each as defined above with a bifunctional compound of the formula (IV)

Z-L-Y  (IV)

in which L and Y are each as defined above and

Z is iodine, fluorine, bromine or tosyl;

(ii) preparation of phenothiazine derivates of the formula (V)

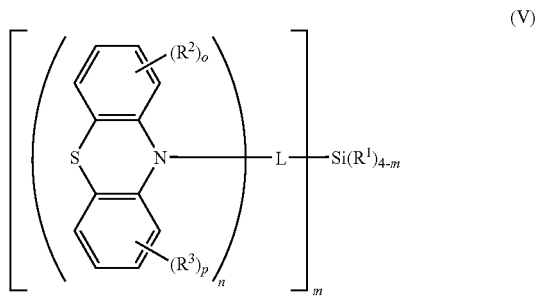

in which the symbols and indices are each as defined above, and m is 1, 2, 3 or 4, preferably 2, 3 or 4, and n is 1 or 2, by reacting the phenothiazine derivate (II) with a haloalkyl/arylsilane of the general formula (VIa) or with an alkoxysilane of the general formula (VIb)

in which $R^8$ is optionally substituted aryl, optionally substituted heteroaryl or optionally substituted alkyl;

Hal is halogen, preferably Cl; and t is 1, 2 or 3; and $R^9$ is alkyl, preferably ethyl or methyl, (iii) preparing the phenothiazine S-oxide or S,S-dioxide derivatives of the formula (I)

by reacting the phenothiazine derivates of the formula (V) with an oxidizing agent.

Suitable preferred radicals and groups of the compounds used in the process according to the invention correspond to the preferred radicals and groups specified above for the compounds of the formula I.

Step (i)

The phenothiazines or phenothiazine derivatives of the formula (III) used to prepare the phenothiazine derivatives of the formula (II) are commercially available or can be prepared by processes known to those skilled in the art. The bifunctional compounds of the formula (IV) which are reacted with the phenothiazines or phenothiazine derivatives of the formula (III) are likewise commercially available or can be prepared by processes known to those skilled in the art.

The substitution of the nitrogen atom of the phenothiazine or phenothiazine derivative of the formula (III) with the bifunctional compound of the formula (IV) (N-alkylation or N-arylation) carried out in step (i) of the process according to the invention is preferably effected in the presence of bases which are known to those skilled in the art. The bases are preferably alkali metal or alkaline earth metal hydroxides such as NaOH, KOH, Ca(OH)$_2$, alkali metal hydrides such as NaH, KH, alkali metal amides such as NaNH$_2$, alkali metal or alkaline earth metal carbonates such as K$_2$CO$_3$, or alkali metal alkoxides, such as NaOMe, NaOEt. In addition, mixtures of the aforementioned bases are suitable. Particular preference is given to NaOH, KOH or NaH. Particularly preferred bases are NaH and K$_2$CO$_3$.

The N-alkylation (described, for instance, in M. Tosa et al., Heterocycl. Communications, Vol. 7, No. 3, 2001, p. 277-282) or N-arylation (described, for instance, in H. Gilman and D. A. Shirley, J. Am. Chem. Soc. 66 (1944) 888; D. Li et al., Dyes and Pigments 49 (2001) 181-186) is preferably performed in a solvent. Suitable solvents are, for example, polar aprotic solvents such as dimethyl sulfoxide, dimethyl formamide or alcohols. It is likewise possible to use an excess of the alkyl halide or aryl halide used as a solvent, preference being given to the use of an excess of alkyl iodides or aryl iodides. The reaction may additionally be performed in a nonpolar aprotic solvent, for example toluene, when a phase transfer catalyst, for example tetra-n-butylammonium hydrogen sulfate is present (as disclosed, for example, in I. Gozlan et al., J. Heterocycl. Chem. 21 (1984) 613-614).

The N-arylation can, though, also be effected by copper-catalyzed coupling of the compound of the formula (III) with an aryl halide, preferably an aryl iodide (Ullmann reaction). A suitable process for N-arylation of phenothiazine in the presence of copper bronze is disclosed, for example, in H. Gilman et al., J. Am. Chem. Soc. 66 (1944) 888-893.

The molar ratio of the compound of the formula (III) to the bifunctional compound of the formula (IV) is generally from 1:1 to 1:2, preferably from 1:1 to 1:1.5.

The N-alkylation or N-arylation is performed typically at standard pressure and within a temperature range from 0 to 220° C. or to the boiling point of the solvent used. The reaction time generally varies from 0.5 to 48 hours.

The suitable conditions for the N-alkylation or N-arylation of the compound of the formula (III) can be determined in each case in preliminary experiments by the person skilled in the art without any problems. For example, the progress of the N-alkylation or N-arylation can be monitored with analytical methods, for instance by IR spectroscopy.

The resulting crude product is generally worked up by processes known to those skilled in the art.

Step (ii)

In step (ii), phenothiazine derivatives of the formula (V) are prepared by reacting the phenothiazine derivatives of the formula (II) prepared in step (i) with a haloalkyl/arylsilane of the formula (VIa) or an alkoxysilane of the formula (VIb). The haloalkyl/arylsilanes of the formula (VIa) and the alkoxysilanes of the formula (VIb) are generally commercially available or can be prepared by processes known to those skilled in the art. Suitable haloalkyl/arylsilanes are haloalkylsilanes, haloarylsilanes or mixed haloalkyl/haloarylsilanes. The suitable haloalkyl/arylsilane used may, for example, be dichlorodimethylsilane, dichlorodiphenylsilane, dichloromethylphenylsilane or tetrachlorosilane.

The phenothiazine or phenothiazine derivative of the formula (II) is reacted with the haloalkyl/arylsilane of the formula (VIa) or the alkoxysilane (VIb) generally in the presence of a metal or of a metal salt such as magnesium or BuLi (m, sec, tert). Suitable reaction conditions for the reaction in step (ii) of the process according to the invention are known to those skilled in the art or can be determined easily by the person skilled in the art.

Typically, the process in step (ii) is performed at standard pressure. The temperature is generally from −78° C. to +100° C. The reaction time is generally from 1 hour to 24 hours.

The resulting crude product is generally worked up by processes known to those skilled in the art.

Step (iii)

In step (iii) of the process according to the invention, the inventive phenothiazine S-oxide or S,S-dioxide derivatives of the formula (I) are prepared proceeding from the phenothiazine derivatives of the formula (V) prepared in step (ii). The inventive phenothiazine S-oxide or S,S-dioxide derivatives of the formula (I) are obtained by reacting the phenothiazine derivatives of the formula (V) with an oxidizing agent. Suitable oxidizing agents depend on whether phenothiazine S-oxide or phenothiazine S,S-dioxide derivatives are prepared. Oxidizing agents suitable for preparing the particular derivatives are known to those skilled in the art. Examples of suitable oxidizing agents are specified below.

Suitable processes for oxidizing the phenothiazines to the phenothiazine S-oxides and phenothiazine S,S-dioxides used in accordance with the invention are known to those skilled in the art and are specified, for example, in M. Tosa et al. Heterocyclic Communications, Vol. 7, No. 3, 2001, p. 277 to 282.

The oxidation to phenothiazine S-oxide derivatives is effected, for example, by means of $H_2O_2$ in ethanol, ethanol-acetone mixtures or oxalic acid, by means of ammonium persulfate, nitric acid, nitrous acid, inorganic nitrogen oxides, if appropriate together with (atmospheric) oxygen, $NO^+BF_4^-/O_2$, $CrO_3$ in pyridine, ozone, tetramethyloxirane, perfluoroalkyloxaziridines or by means of electrochemical methods. In addition, the oxidation of the correspondingly functionalized phenothiazines of the formula V to the corresponding phenoxazine S-oxide derivatives of the formula I can be effected by means of m-chloroperbenzoic acid in $CH_2Cl_2$ at temperatures of from 0 to 5° C. or by means of a mixture of fuming nitric acid and glacial acetic acid in $CCl_4$ (see, for instance, M. Tosa et al. Heterocyclic Communications, Vol. 7, No. 3, 2001, p. 277 to 282).

The oxidation to phenothiazine S,S-dioxide derivatives is effected, for example, by means of peracids such as peracetic acid, which is obtainable, for example, from $H_2O_2$ and AcOH, or m-chloroperbenzoic acid, sodium perborate, NaOCl or heavy metal systems such as $KMnO_4/H_2O$, $Et_3PhN^+MnO_4^-$ in organic media, $OsO_4$/N-methylmorpholine N-oxide. For instance, the oxidation of the correspondingly functionalized phenothiazines of the formula V to the corresponding phenothiazine S,S-dioxide derivatives of the formula I can be effected by means of an aqueous solution of $KMnO_4$ and $C_{16}H_{35}N(CH_3)_3^+Cl^-$ in $CHCl_3$ at room temperature, or by means of m-chloroperbenzoic acid in $CH_2Cl_2$ at room temperature (see, for instance, M. Tosa et al. Heterocyclic Communications, Vol. 7, No. 3, 2001, p. 277-282).

To prepare the phenothiazine S,S-dioxide derivatives, the phenothiazine derivative of the formula V and the oxidizing agent, preferably m-chloroperbenzoic acid, are used in a molar ratio of generally from 1:1.8 to 1:4, preferably from 1:1.9 to 1:3.5, more preferably from 1:1.9 to 1:3.

To prepare phenothiazine S-oxide derivatives, the phenothiazine derivative of the formula V and the oxidizing agent are used in a molar ratio of generally from 1:0.8 to 1:1.5, preferably from 1:1 to 1:1.3. Oxidizing agents with which no further oxidation to the corresponding S,S-dioxide derivatives is effected, for example $H_2O_2$, can be used in a greater excess than that specified above in relation to the phenothiazine derivative.

The oxidation is effected generally in a solvent, preferably in a solvent selected from the group consisting of halogenated hydrocarbons and dipolar aprotic solvents.

Examples of the former and the latter are, respectively, methylene chloride, and acetonitrile and sulfolane.

Depending on the oxidizing agent, the oxidation to the phenothiazine S-oxide derivatives is effected typically at standard pressure within a temperature range from −10° C. to +50° C., and the oxidation to the phenothiazine S,S-dioxide derivatives typically at standard pressure within a temperature range from 0 to +100° C. The reaction time of the oxidation is generally from 0.25 to 24 hours.

The suitable conditions for the oxidation of the particular phenothiazine derivatives to the corresponding phenothiazine S-oxide or phenothiazine S,S-dioxide derivatives can, though, be determined in each case in preliminary experiments without any problems by the person skilled in the art. For example, the progress of the oxidation can be monitored by analytical methods, for instance by IR spectroscopy.

In a preferred variant, the phenothiazine S-oxide derivatives of the formula I are prepared by oxidizing the corresponding phenothiazine derivatives of the formula V with m-chloroperbenzoic acid as the oxidizing agent in $CH_2Cl_2$ at from 0 to 20° C.

The phenothiazine S,S-dioxide derivatives of the formula I are prepared preferably by oxidizing the corresponding phenothiazine derivatives of the formula V with m-chloroperbenzoic acid as the oxidizing agent in $CH_2Cl_2$ at from 0 to 40° C.

The resulting phenothiazine S-oxides and phenothiazine S,S-dioxides are isolated and worked up by processes known to those skilled in the art.

The inventive compounds of the formula I can be obtained in high purity and in good yields with the aid of the process according to the invention. The high purity is, if appropriate, achieved by purifying the product obtained in the process according to the invention, for example by recrystallization.

The compounds of the formula (I) are outstandingly suitable for use as matrix materials in organic light-emitting diodes. In particular, they are suitable as matrix materials in the light-emitting layer of the OLEDs, in which case the light-emitting layer comprises, as emitter compounds, preferably one or more triplet emitters.

The compounds of the formula (I) are additionally suitable as blocker materials, especially as blocker materials in OLEDs, preference being given to using them as blocker materials for triplet emitters. The compounds of the formula (I) may—depending on their substitution pattern—be used as hole/exciton blockers or electron/exciton blockers, as has already been stated above.

The present invention therefore further provides an OLED comprising at least one compound of the formula (I). Preference is given to using the compound of the formula (I) in one embodiment as a matrix material, in which case the matrix material is more preferably used together with a triplet emitter. In a further embodiment, the compound of the formula (I) is preferably used as a blocker material, more preferably as a blocker material for triplet emitters.

In addition, the compounds of the formula (I) may be used in OLEDs both as a matrix material and as a blocker material. In this case, the matrix material and the blocker material may be the same or different compounds of the formula (I).

The present invention further provides a light-emitting layer comprising at least one inventive compound of the formula (I) and at least one emitter compound, in which case the emitter compound is preferably a triplet emitter.

In a further embodiment, the present invention relates to the use of the compounds of the formula (I) as blocker materials in OLEDs. In addition, an OLED may comprise the compounds of the formula (I) both as matrix materials and as blocker materials.

The present invention further relates to the use of the inventive compounds of the formula (I) in OLEDs, preferably as matrix materials, especially as matrix materials for emitter compounds, in which case the emitter compounds are more preferably triplet emitters.

The use of the inventive compounds of the formula (I) as matrix materials in the light-emitting layer of an OLED likewise forms a further part of the subject matter of the present invention.

The use of the compounds of the formula I as matrix materials and/or blocker materials in this context is not intended to rule out that these compounds themselves also emit light. The matrix materials and/or blocker materials used in accordance with the invention, however, have the effect that, in the case of compounds which are used as emitters in OLEDs, an increase in the luminance and quantum yield compared to otherwise customary matrix materials and/or blocker materials can be achieved when they are embedded into the matrix material or when the OLEDs comprise the compounds of the formula (I) as a blocker material.

Many of the emitter compounds used with preference are based on metal complexes, and especially the complexes of the metals Ru, Rh, Ir, Pd and Pt, in particular the complexes of Ir, have gained significance. The compounds of the formula I used in accordance with the invention are suitable particularly as matrix materials and/or blocker materials for emitters based on such metal complexes. In particular, they are suitable for use as matrix materials and/or blocker materials together with complexes of Ru, Rh, Ir, Pd and Pt, more preferably for use together with complexes of Ir.

Suitable metal complexes for use together with the compounds of the formula I as matrix materials and/or blocker materials in OLEDs are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1 and WO 2006/056418.

Further suitable metal complexes are the commercially available metal complexes tris(2-phenylpyridin)iridium(III), tris(2-(4-tolyl)pyridinato-N,C$^{2'}$)iridium(III), tris(1-phenyl-isoquinoline)iridium(III), bis(2-(2'-benzothienyl)pyridinato-N,C$^{3'}$)(acetyl-acetonato)iridium(III), iridium(III) bis(2-(4,6-difluorophenyl)pyridinato-N,C$^{2}$)picolinate, iridium(III) bis(1-phenylisoquinoline)(acetylacetonate), iridium(III) bis(dibenzo[f,h]quinoxaline)(acetylacetonate), iridium(III) bis(2-methyldi-benzo[f,h]quinoxaline)(acetylacetonate) and tris(3-methyl-1-phenyl-4-trimethylacetyl-5-pyrazoline)terbium(III).

In addition, the following commercially available materials are suitable: tris(dibenzoylacetonato)mono(phenanthroline)europium(III), tris(dibenzoylmethane)-mono(phenanthroline)europium(III), tris(dibenzoylmethane)mono(5-aminophenan-throline)europium(III), tris(di-2-naphthoylmethane)mono(phenanthroline)europium(III), tris(4-bromobenzoylmethane)mono(phenanthroline)europium (III), tris(di(biphenyl-methane))mono(phenanthroline) europium(III), tris(dibenzoylmethane)mono(4,7-diphenylphenanthroline)europium(III), tris(dibenzoylmethane)mono(4,7-di-methyl-phenanthroline) europium(III), tris(dibenzoylmethane)mono(4,7-dimethylphenanthroline-disulfonic acid)europium(III) disodium salt, tris[di(4-(2-(2-ethoxyethoxy)ethoxy)benzoylmethane)]mono(phenanthroline)europium(III) and tris[d][4-(2-(2-ethoxyethoxy)-ethoxy)benzoylmethane)]mono(5-aminophenanthroline)europium(III).

In a preferred embodiment of the present invention, the inventive compounds of the formula I are used in the light-emitting layer as a matrix material together with carbene complexes as triplet emitters, i.e. particularly preferred triplet emitters are carbene complexes. Suitable carbene complexes are known to those skilled in the art and are specified in some of the aforementioned applications and below. In a further preferred embodiment, the inventive compounds of the formula (I) are used as blocker material together with carbene complexes as triplet emitters. The inventive compounds may additionally be used both as matrix materials and as blocker materials together with carbene complexes as triplet emitters.

Suitable metal complexes for use together with the compounds of the formula I as matrix materials and/or blocker materials in OLEDs are thus, for example, also carbene complexes as described in WO 2005/019373 A2, WO 2006/056418 A2 and WO 2005/113704, and in the prior European applications EP 06 112 228.9 and EP 06 112 198.4, which were yet to be published at the priority date of the present application. Reference is hereby made explicitly to the disclosure of the WO and EP applications mentioned, and these disclosures shall be incorporated into the content of the present application. In particular, suitable metal complexes for use together with the compounds of the formula I as matrix materials and/or blocker materials in OLEDs comprise carbene ligands of the following structures disclosed, inter alia, in WO 2005/019373 A2 (the designation of the variables used hereinafter was adopted from the application WO 2005/019373 A2; with regard to the more specific definition of the variables, reference is made explicitly to this application):

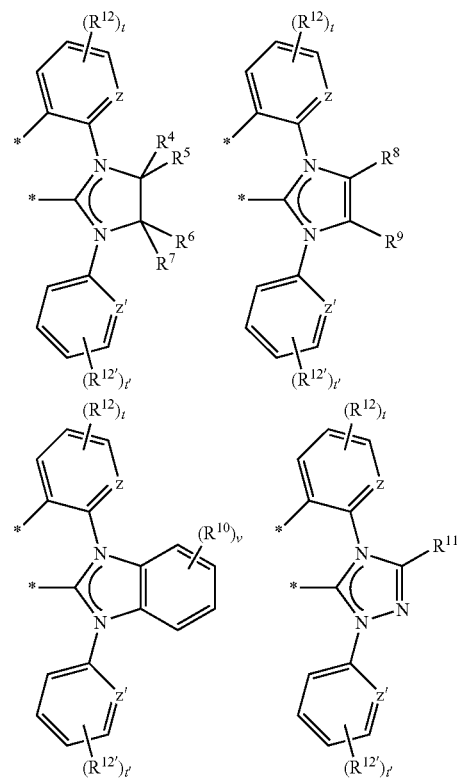

in which:
* denotes the attachment sites of the ligands to the metal center;
z, z' are the same or different and are each CH or N;
$R^{12}$, $R^{12'}$ are the same or different and are each an alkyl, aryl, heteroaryl or alkenyl radical, preferably an alkyl or aryl radical, or in each case 2 $R^{12}$ or $R^{12'}$ radicals together form a fused ring which may optionally comprise at least one heteroatom, preferably N; preferably in each case 2 $R^{12}$ or $R^{12'}$ radicals together form a fused aromatic $C_6$ ring, where one or more further aromatic rings may be fused to this preferably six-membered aromatic ring, any conceivable fusion being possible, and the fused radicals may in turn be substituted; or $R^{12}$ or $R^{12'}$ is a radical with donor or acceptor action, preferably selected from the group consisting of halogen radicals, preferably F, Cl, Br, more preferably F; alkoxy, aryloxy, carbonyl, ester, amino groups, amide radicals, CHF$_2$, CH$_2$F, CF$_3$, CN, thio groups and SCN;

t and t' are the same or different, preferably the same, and are each from 0 to 3, where, when t or t' is >1, the R$^{12}$ or R$^{12'}$ radicals may be the same or different; t or t' is preferably 0 or 1; the R$^{12}$ or R$^{12'}$ radical is, when t or t' is 1, in the ortho-, meta- or para-position to the bonding site to the nitrogen atom adjacent to the carbene carbon atom;

R$^4$, R$^5$, R$^6$,

R$^7$, R$^8$, R$^9$ and R$^{11}$ are each hydrogen, alkyl, aryl, heteroaryl, alkenyl or a substituent having donor or acceptor action, preferably selected from halogen radicals, preferably F, Cl, Br, more preferably F, alkoxy radicals, aryloxy radicals, carbonyl radicals, ester radicals, amine radicals, amide radicals, CH$_2$F groups, CHF$_2$ groups, CF$_3$ groups, CN groups, thio groups and SCN groups, preferably hydrogen, alkyl, heteroaryl or aryl, R$^{10}$ is alkyl, aryl, heteroaryl or alkenyl, preferably alkyl, heteroaryl or aryl, or in each case 2 R$^{10}$ radicals together form a fused ring which may optionally comprise at least one heteroatom, preferably nitrogen; preferably in each case 2 R$^{10}$ radicals together form a fused aromatic C$_6$ ring, where one or more further aromatic rings may optionally be fused to this preferably six-membered aromatic ring, any conceivable fusion being possible, and the fused radicals may in turn be substituted; or R$^{10}$ is a radical having donor or acceptor action, preferably selected from the group consisting of halogen radicals, preferably F, Cl, Br, more preferably F; alkoxy, aryloxy, carbonyl, ester, amino groups, amide radicals, CHF$_2$, CH$_2$F, CF$_3$, CN, thio groups and SCN v is from 0 to 4, preferably 0, 1 or 2, most preferably 0, where, when v is 0, the four carbon atoms of the aryl radical in formula c, which are optionally substituted by R$^{10}$, bear hydrogen atoms.

In particular, suitable metal complexes for use together with the compounds of the formula I as matrix materials and/or blocker materials in OLEDs comprise Ir-carbene complexes of the following structures disclosed in WO 2005/019373 A2:

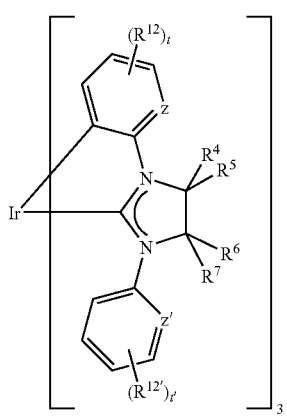

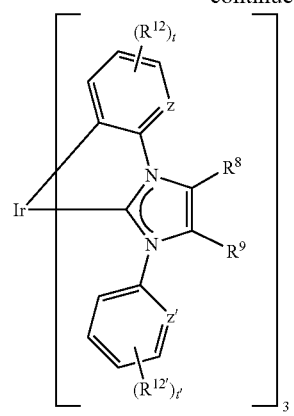

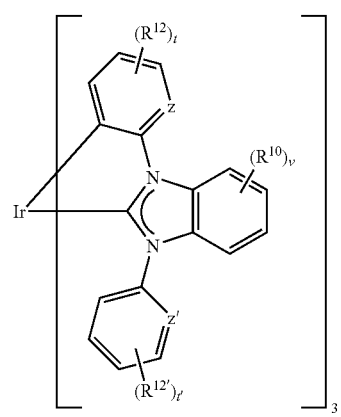

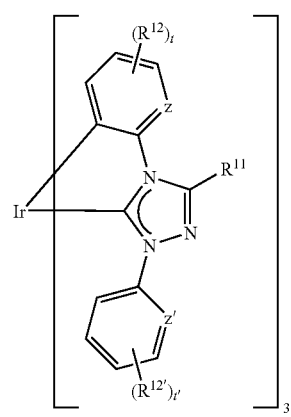

where the variables are each as already defined above.

Further suitable metal complexes for use together with the compounds of the formula I as matrix materials and/or blocker materials in OLEDs are especially also structures disclosed in WO 2006/056418 A2 (the designation of the variables used hereinafter was adopted from the application WO 2006/056418 A2; with regard to the more exact definition of the variables, reference is made explicitly to this application):

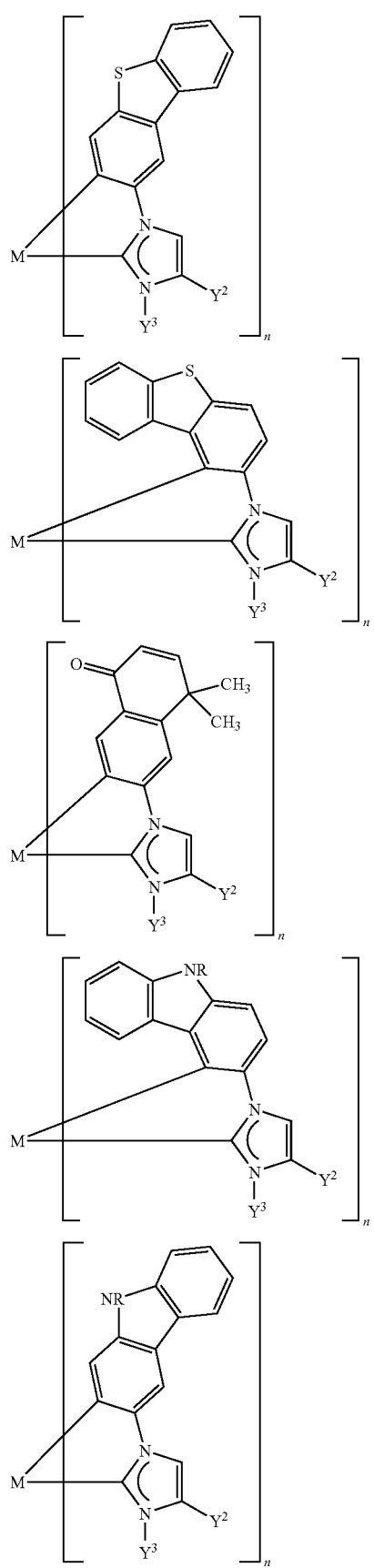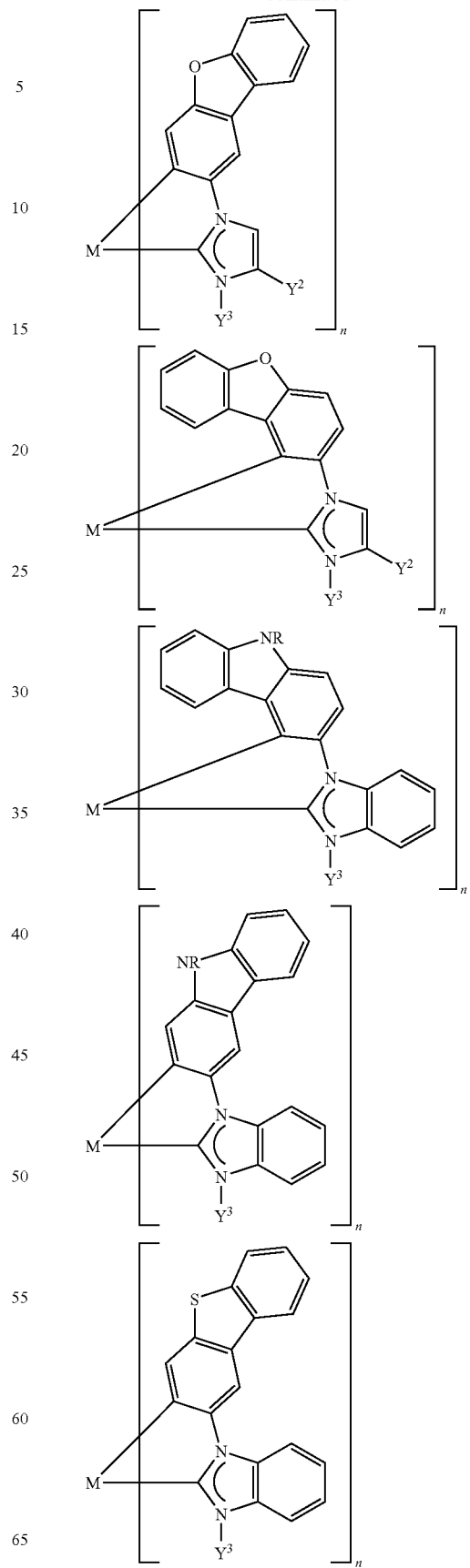

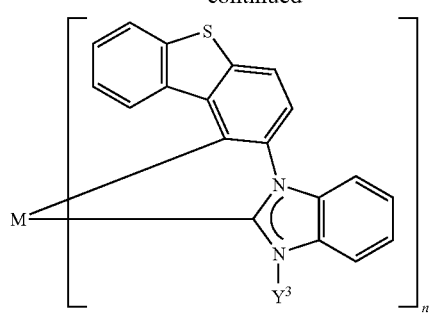
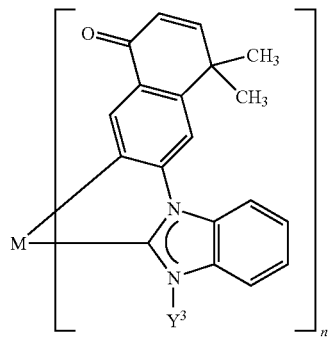
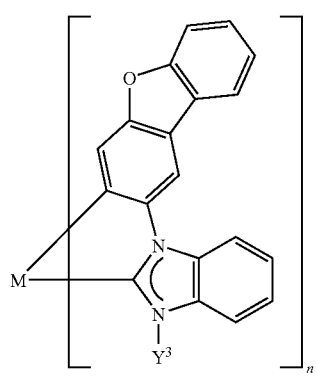
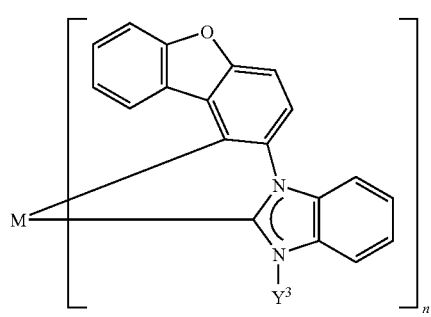
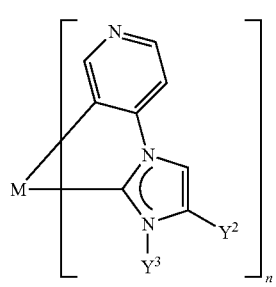
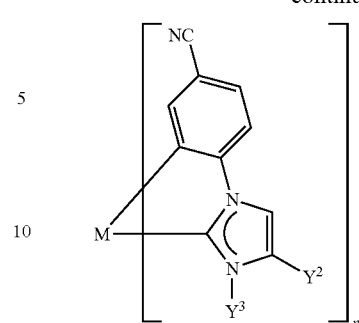
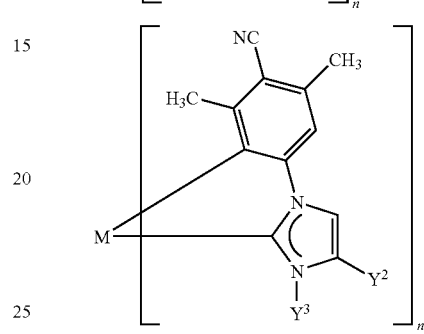
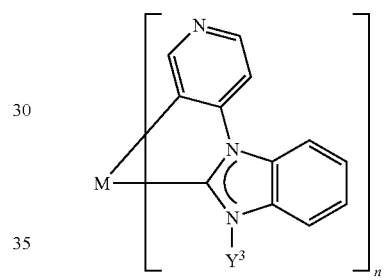
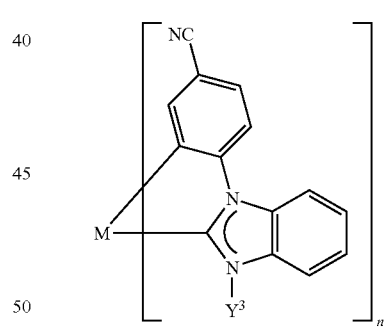
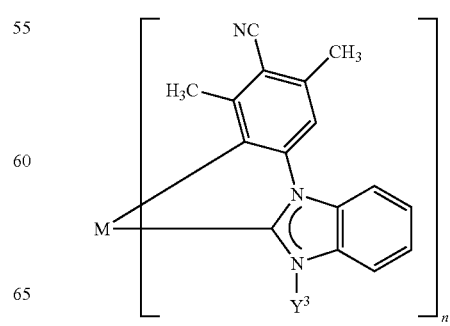

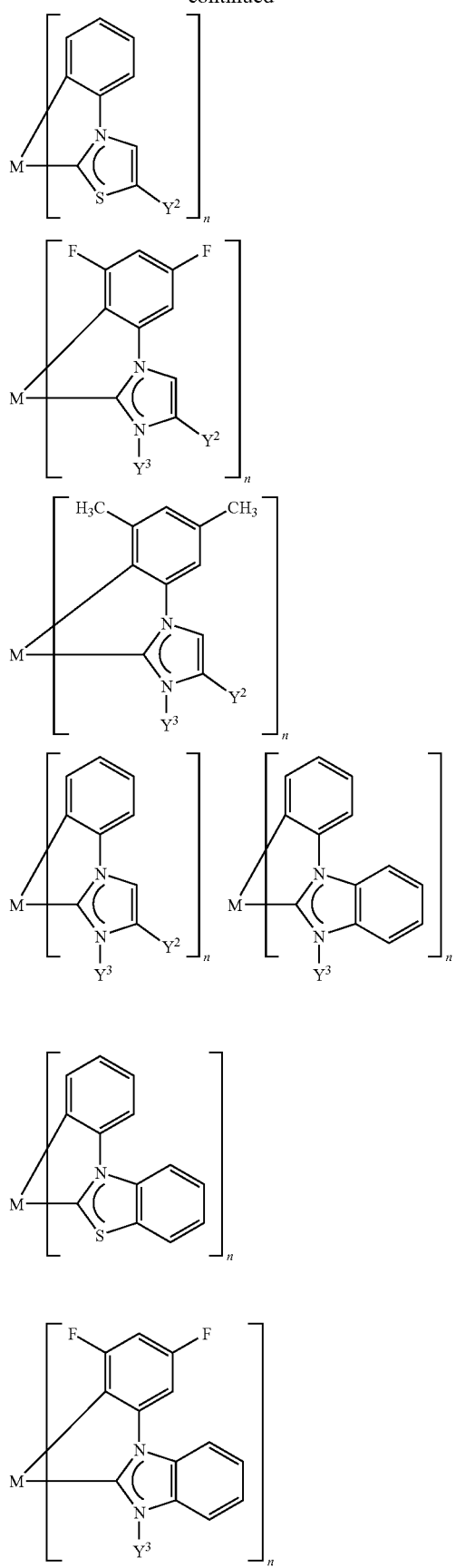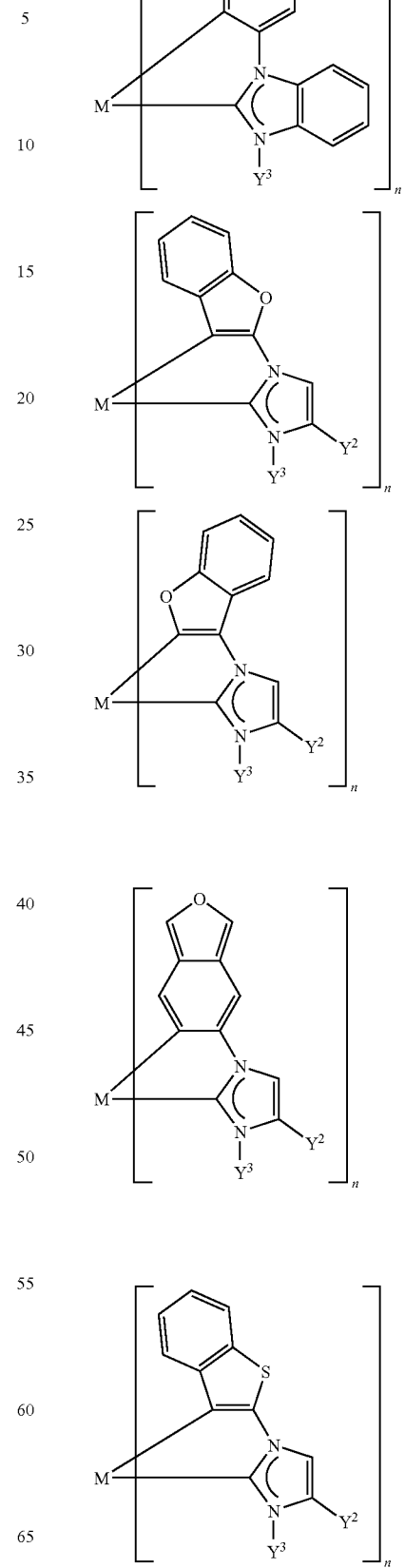

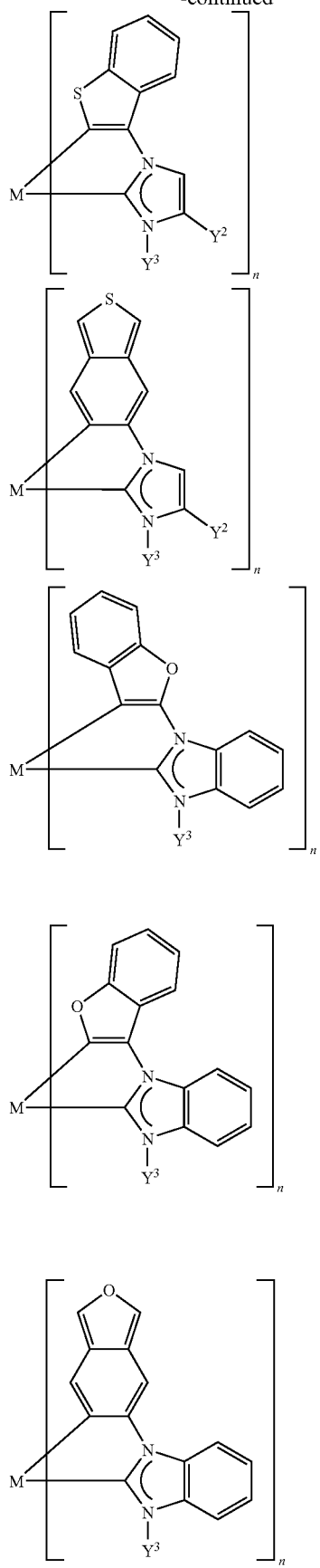
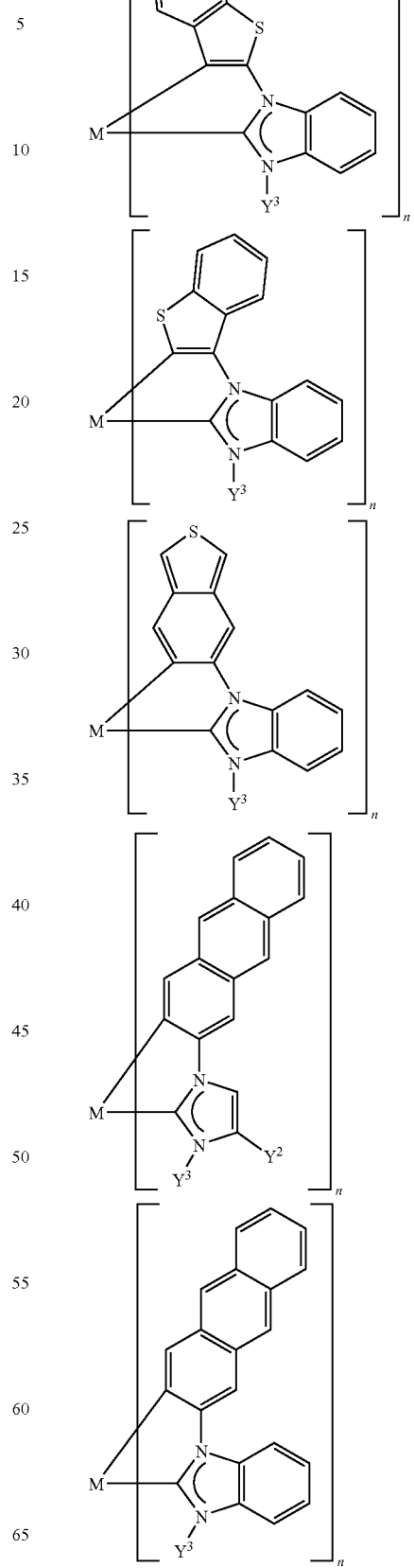

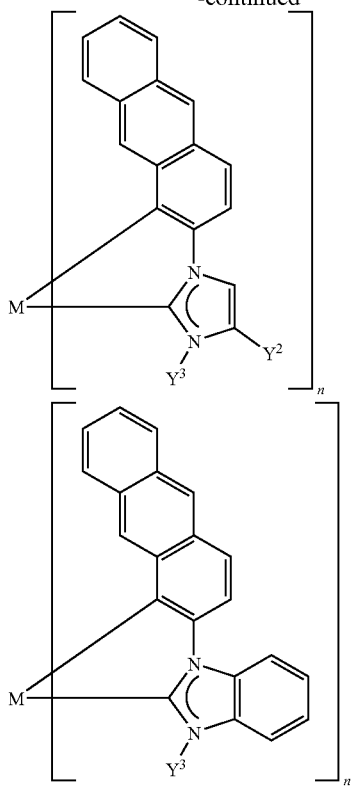

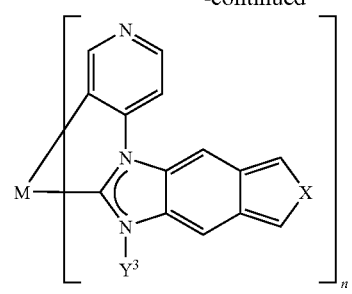

X = O, S

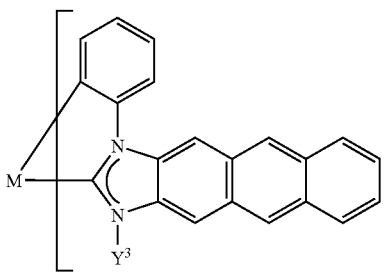

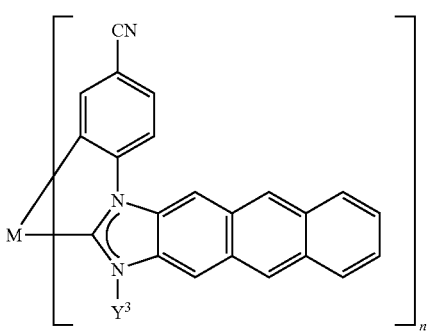

in which M is Ru(III), Rh(III), Ir(III), Pd(II) or Pt(II), n assumes the value of 3 for Ru(III), Rh(III) and Ir(III), and the value of 2 for Pd(II) and Pt(II), and $Y^2$ and $Y^3$ are each hydrogen, methyl, ethyl, n-propyl, isopropyl or tert-butyl. M is preferably Ir(III) with n equal to 3. $Y^3$ is preferably methyl, ethyl, n-propyl, isopropyl or tert-butyl.

Further suitable metal complexes for use together with the compounds of the formula I as matrix materials and/or blocker materials in OLEDs are especially also

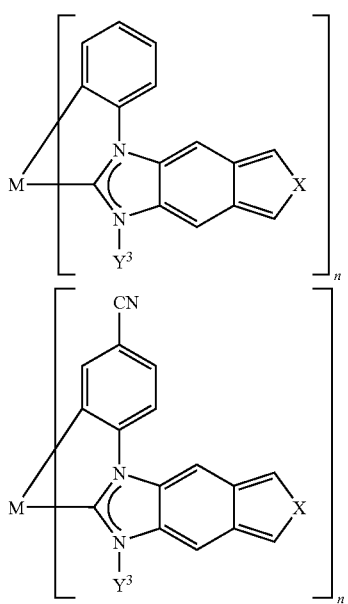

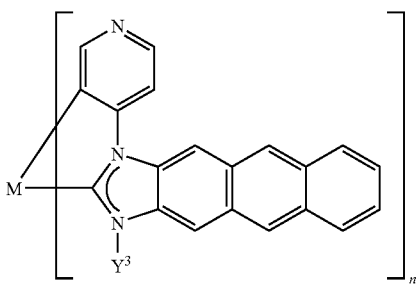

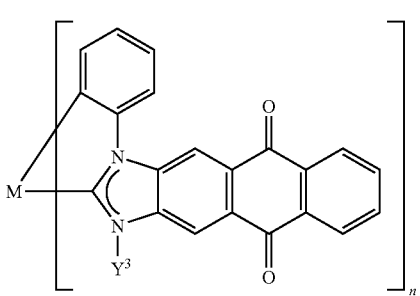

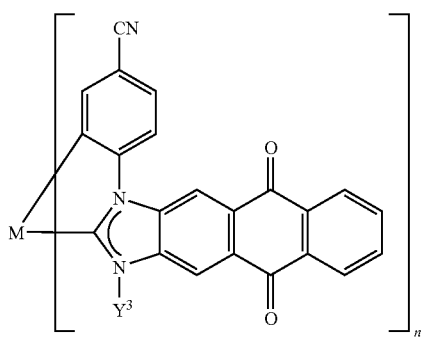

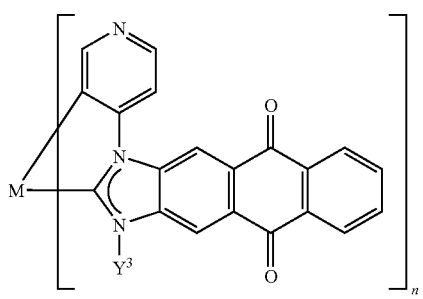

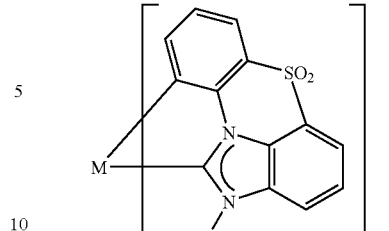

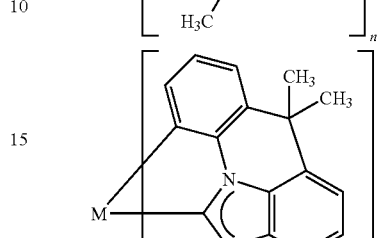

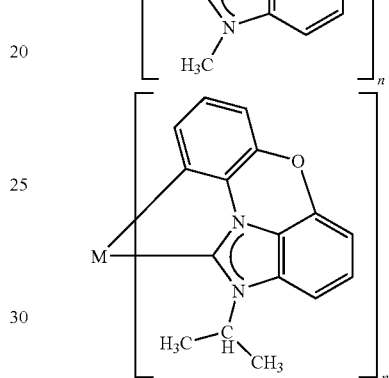

in which M is Ru(III), Rh(III), Ir(III), Pd(II) or Pt(II), n assumes the value of 3 for Ru(III), Rh(III) and Ir(III), and the value of 2 for Pd(II) and Pt(II), and $Y^3$ is hydrogen, methyl, ethyl, n-propyl, isopropyl or tert-butyl. M is preferably Ir(III) with n equal to 3. $Y^3$ is preferably methyl, ethyl, n-propyl, isopropyl or tert-butyl.

Further suitable metal complexes for use together with the compounds of the formula I as matrix materials and/or blocker materials in OLEDs are especially also:

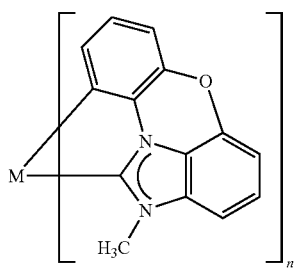

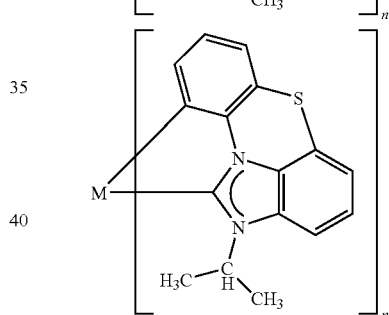

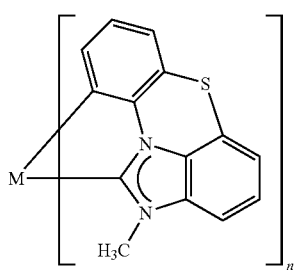

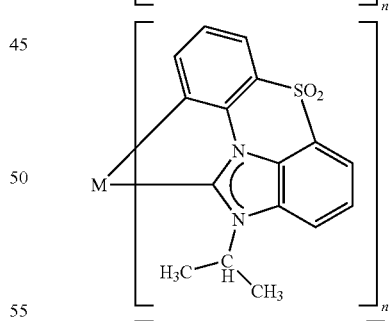

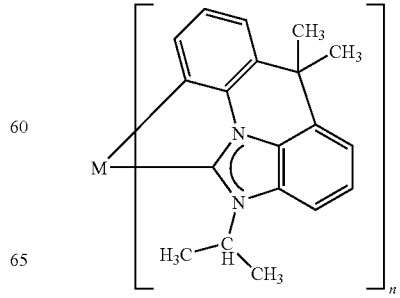

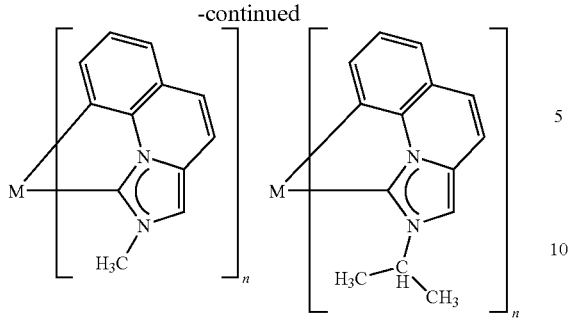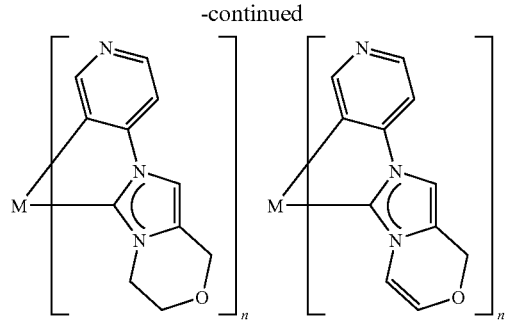
in which M is Ru(III), Rh(III) and especially Ir(III), Pd(II) or Pt(II), n assumes the value of 3 for Ru(III), Rh(III) and Ir(III), and the value of 2 for Pd(II) and Pt(II).
Further suitable metal complexes for use together with the compounds of the formula I as matrix materials and/or blocker materials in OLEDs are especially also:
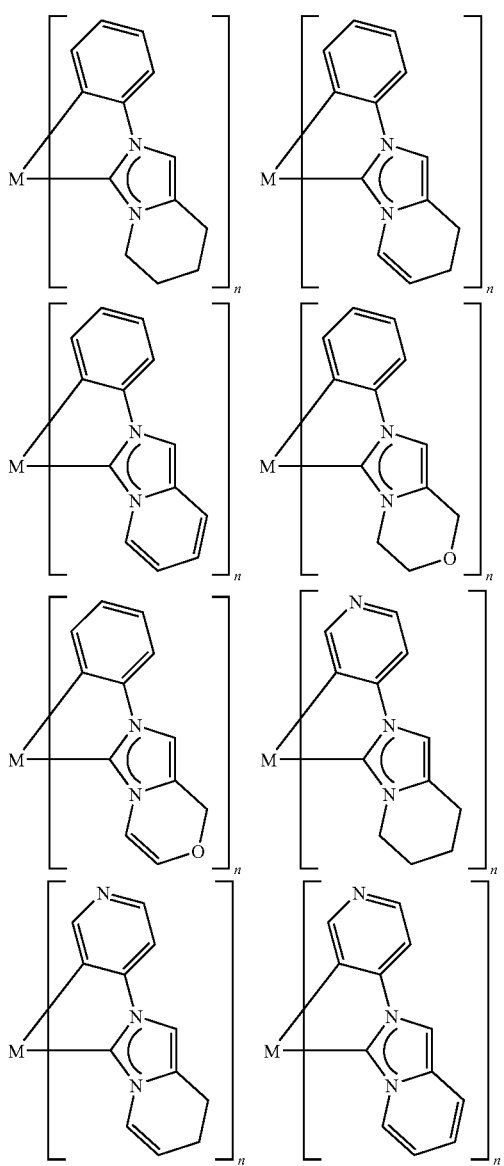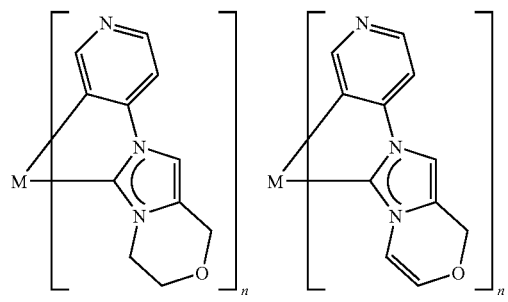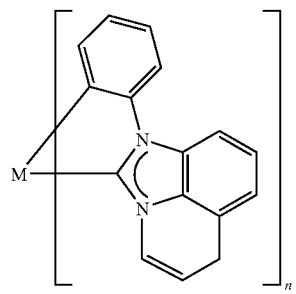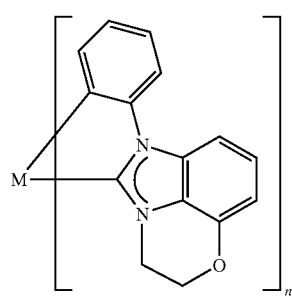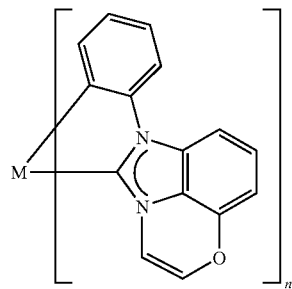

-continued

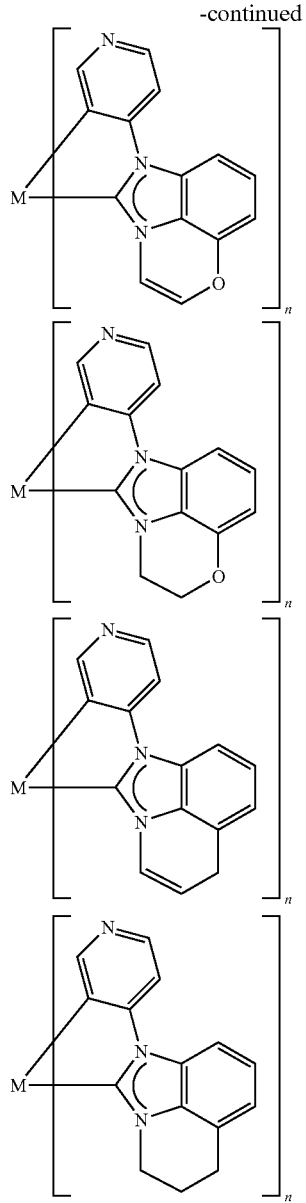

in which M is Ru(III), Rh(III) and especially Ir(III), Pd(II) or Pt(II), n assumes the value of 3 for Ru(III), Rh(III) and Ir(III), and the value of 2 for Pd(II) and Pt(II).

In addition, complexes with different carbene ligands and/or with mono- or dianionic ligands, which may be either mono- or bidentate, are also useful.

With reference to the table which follows, complexes ML′(L″)$_2$ with trivalent metal centers and two different carbene ligands L′ and L″ are specified schematically

| L′ | L″ | L′ | L″ | L′ | L″ | L′ | L″ |
|---|---|---|---|---|---|---|---|
| L$^1$ | L$^2$ | L$^3$ | L$^4$ | L$^7$ | L$^5$ | L$^5$ | L$^3$ |
| L$^1$ | L$^3$ | L$^3$ | L$^5$ | L$^7$ | L$^4$ | L$^5$ | L$^2$ |
| L$^1$ | L$^4$ | L$^3$ | L$^6$ | L$^7$ | L$^3$ | L$^5$ | L$^1$ |
| L$^1$ | L$^5$ | L$^3$ | L$^7$ | L$^7$ | L$^2$ | L$^4$ | L$^3$ |
| L$^1$ | L$^6$ | L$^4$ | L$^5$ | L$^7$ | L$^1$ | L$^4$ | L$^2$ |
| L$^1$ | L$^7$ | L$^4$ | L$^6$ | L$^6$ | L$^5$ | L$^4$ | L$^1$ |
| L$^2$ | L$^3$ | L$^4$ | L$^7$ | L$^6$ | L$^4$ | L$^3$ | L$^2$ |
| L$^2$ | L$^4$ | L$^5$ | L$^6$ | L$^6$ | L$^3$ | L$^3$ | L$^1$ |
| L$^2$ | L$^5$ | L$^5$ | L$^7$ | L$^6$ | L$^2$ | L$^2$ | L$^1$ |
| L$^2$ | L$^6$ | L$^6$ | L$^7$ | L$^6$ | L$^1$ | | |
| L$^2$ | L$^7$ | L$^7$ | L$^6$ | L$^5$ | L$^4$ | | | where M is, for example, Ru(III), Rh(III) or Ir(III), especially Ir(III), and L′ and L″ are, for example, ligands selected from the group of ligands L$^1$ to L$^7$

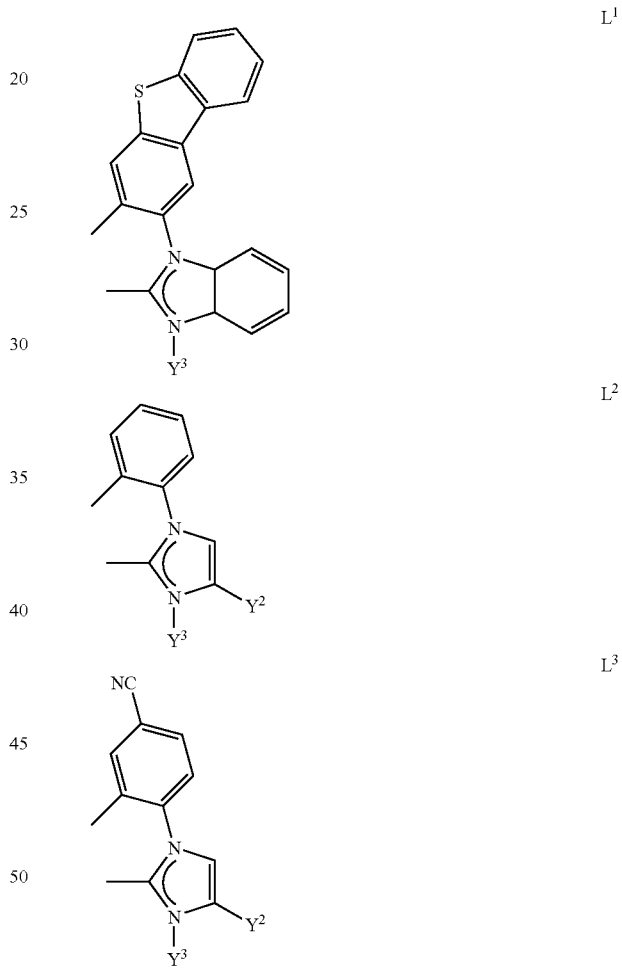

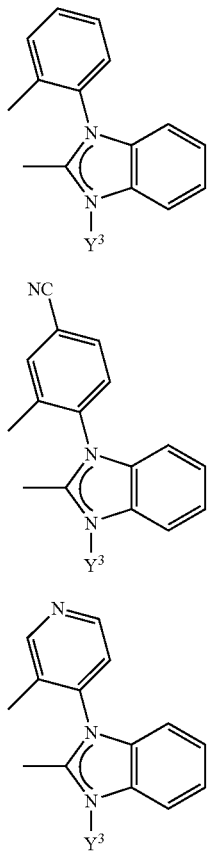

$Y^2$ is hydrogen, methyl, ethyl, n-propyl, isopropyl or tert-butyl, and $Y^3$ is methyl, ethyl, n-propyl, isopropyl or tert-butyl.

One representative of these complexes with different carbene ligands ($L'=L^4$ when $Y^2$=hydrogen and $Y^3$=methyl; $L''=L^2$ when $Y^2$=hydrogen and $Y^3$=methyl) is, for example:

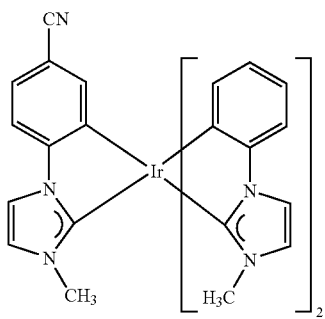

It will be appreciated that, in the complexes used as emitters in the matrix materials and/or together with the complexes of trivalent metal centers (for instance in the case of Ru(III), Rh(III) or Ir(III)) used together with the blocker materials of the formula I, all three carbene ligands may also be different from one another.

Examples of complexes of trivalent metal centers M with ligands L (here monoanionic bidentate ligand) as "spectator ligands" are LML'L", LM(L')$_2$ and L$_2$ML', in which M is, for instance, Ru(III), Rh(III) or Ir(III), especially Ir(III), and L' and L" are each as defined above. For the combination of L' and L" in the complexes LML'L", this gives rise to:

| L' | L" |
|---|---|
| L$^1$ | L$^2$ |
| L$^1$ | L$^3$ |
| L$^1$ | L$^4$ |
| L$^1$ | L$^5$ |
| L$^1$ | L$^6$ |
| L$^1$ | L$^7$ |
| L$^2$ | L$^3$ |
| L$^2$ | L$^4$ |
| L$^2$ | L$^5$ |
| L$^2$ | L$^6$ |
| L$^2$ | L$^7$ |
| L$^3$ | L$^4$ |
| L$^3$ | L$^5$ |
| L$^3$ | L$^6$ |
| L$^3$ | L$^7$ |
| L$^4$ | L$^5$ |
| L$^4$ | L$^6$ |
| L$^4$ | L$^7$ |
| L$^5$ | L$^6$ |
| L$^6$ | L$^7$ |
| L$^6$ | L$^7$ |

Useful ligands L are in particular acetylacetonate and derivatives thereof, picolinate, Schiff bases, amino acids and the bidentate monoanionic ligands specified in WO 02/15645 A1; in particular, acetylacetonate and picolinate are of interest. In the case of the complexes L$_2$ML', the ligands L may be the same or different.

One representative of these complexes with different carbene ligands ($L'=L^4$ when $Y^2$=hydrogen and $Y^3$=methyl; $L''=L^2$ when $Y^2$=hydrogen and $Y^3$=methyl) is, for example:

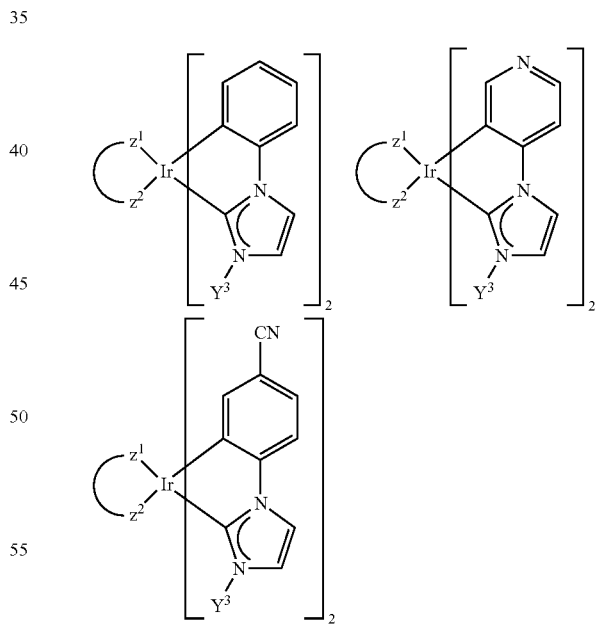

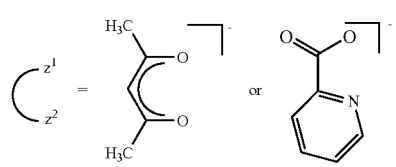

in which $z^1$ and $z^2$ in the symbol

represent the two "teeth" of the ligand L. $Y^3$ is hydrogen, methyl, ethyl, n-propyl, isopropyl or tert-butyl, especially methyl, ethyl, n-propyl or isopropyl.

Further metal complexes especially suitable as emitter compounds for use together with the compounds of the formula I as matrix materials in OLEDs are:

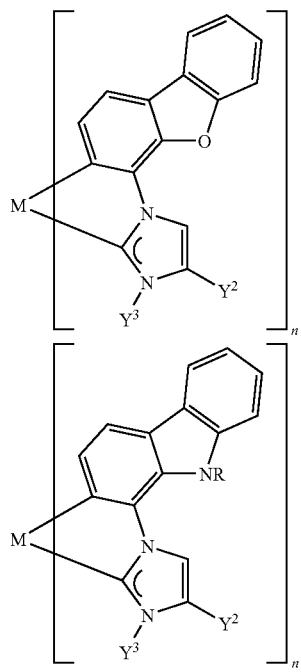

in which R is hydrogen, alkyl or aryl, preferably methyl, ethyl, n-propyl, isopropyl, tert-butyl or phenyl,
and also

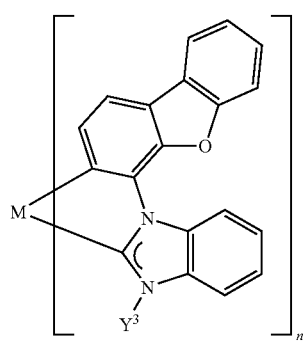

in which M is Ru(III), Rh(III), Ir(III), Pd(II) or Pt(II), n assumes the value of 3 in the case that M is Ru(III), Rh(III) and Ir(III), and assumes the value of 2 in the case that M is Pd(II) and Pt(II), and $Y^2$ and $Y^3$ are each hydrogen, methyl, ethyl, n-propyl, isopropyl or tert-butyl. M is preferably Ir(III) with n equal to 3. $Y^3$ is preferably methyl, ethyl, n-propyl, isopropyl or tert-butyl.

In addition, the following specific metal complexes are suitable for use in OLEDs, especially as emitter compounds, together with the compounds of the formula I as matrix materials:

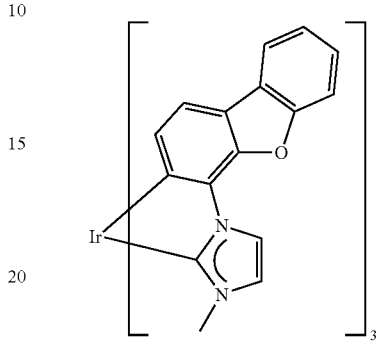

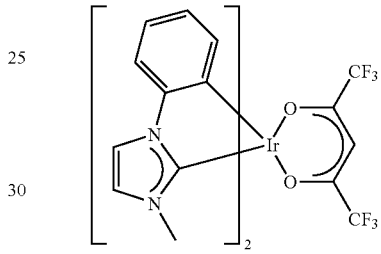

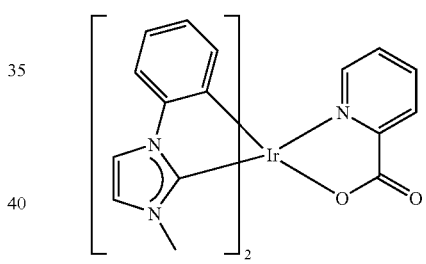

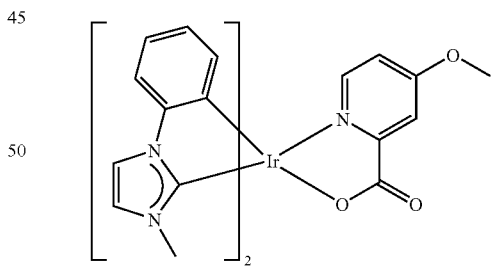

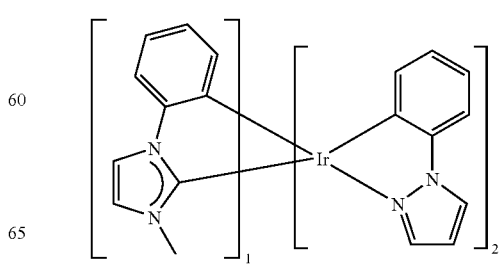

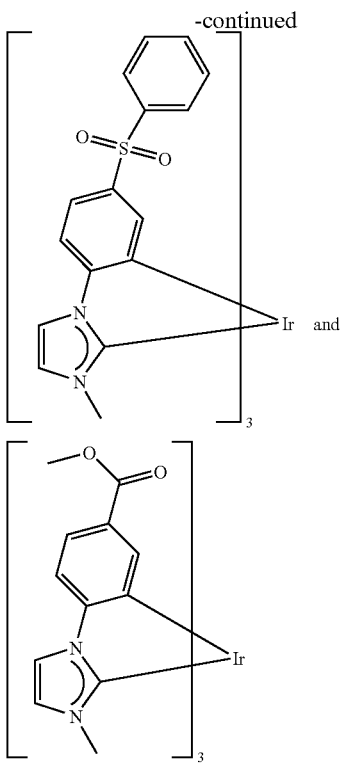

The aforementioned carbene complexes are prepared by processes known to those skilled in the art. The stochiometries and reaction conditions can be determined without any problem by the person skilled in the art on the basis of the aforementioned patent applications relating to carbene complexes and their preparation processes. In addition, in the example part of the present application, processes are specified for preparing some of the aforementioned carbene complexes. The carbene complexes which are not described explicitly in the examples may be prepared in analogy to the processes described in the example part.

When at least one inventive compound of the formula (I) is used together with an emitter compound, preferably together with a triplet emitter, in the light-emitting layer of an OLED, which is particularly preferred, the proportion of the at least one compound of the formula (I) in the light-emitting layer is generally from 10 to 99% by weight, preferably from 50 to 99% by weight, more preferably from 70 to 97% by weight. The proportion of the emitter compound in the light-emitting layer is generally from 1 to 90% by weight, preferably from 1 to 50% by weight, more preferably from 3 to 30% by weight, the proportions of the at least one compound of the formula (I) and of the at least one emitter compound generally adding up to 100% by weight. However, it is also possible that the light-emitting layer, as well as the at least one compound of the formula (I) and the at least one emitter compound, comprises further substances, for example further dilution material, suitable dilution material being specified below.

Organic light-emitting diodes (OLEDs) are in principle constructed from several layers, for example:
1. Anode
2. Hole-transporting layer
3. Light-emitting layer
4. Electron-transporting layer
5. Cathode Layer sequences different from the aforementioned construction are also possible, which are known to those skilled in the art. For example, it is possible that the OLED does not have all of the layers mentioned; for example, an OLED comprising layers (1) (anode), (3) (light-emitting layer) and (5) (cathode) is likewise suitable, the functions of the layers (2) (hole-transporting layer) and (4) (electron-transporting layer) being assumed by the adjacent layers. OLEDs which have the layers (1), (2), (3) and (5) or the layers (1), (3), (4) and (5) are likewise suitable.

The compounds of the formula I may be used as charge-transporting, especially electron-transporting, materials, but they also preferably find use as matrix materials in the light-emitting layer or as the hole/exciton blocker layer. Compounds of the formula (I) substituted by electron-donating substituents may additionally be used as the electron/exciton blocker layer.

The inventive compounds of the formula I may be present as the sole matrix material—without further additives—in the light-emitting layer. However, it is likewise possible that, in addition to the compounds of the formula I used in accordance with the invention, further compounds are present in the light-emitting layer. For example, a fluorescent dye may be present in order to modify the emission color of the emitter molecule present. In addition, a dilution material may be used. This dilution material may be a polymer, for example poly(N-vinylcarbazole) or polysilane. However, the dilution material may likewise be a small molecule, for example 4,4'-N,N'-dicarbazolebiphenyl (CBP=CDP) or tertiary aromatic amines. Where a dilution material is used, the proportion of the compounds of the formula I used in accordance with the invention in the light-emitting layer is generally always still at least 40% by weight, preferably from 50 to 100% by weight, based on the total weight of the compounds of the formula I and diluents.

The individual layers of the OLED among those specified above may in turn be formed from 2 or more layers. For example, the hole-transporting layer may be formed from a layer into which holes are injected from the electrode, and a layer which transports the holes away from the hole-injecting layer into the light-emitting layer. The electron-transporting layer may likewise consist of a plurality of layers, for example a layer in which electrons are injected by the electrode, and a layer which receives electrons from the electron-injecting layer and transports them into the light-emitting layer. These layers are in each case selected according to factors such as energy level, thermal resistance and charge carrier mobility, and also energy difference of the layers mentioned from the organic layers or the metal electrodes. The person skilled in the art is capable of selecting the construction of the OLEDs such that it is matched optimally to the organic compounds used in accordance with the invention as emitter substances.

In order to obtain particularly efficient OLEDs, the HOMO (highest occupied molecular orbital) of the hole-transporting layer should be matched to the work function of the anode, and the LUMO (lowest unoccupied molecular orbital) of the electron-transporting layer should be matched to the work function of the cathode.

The anode (1) is an electrode which provides positive charge carriers. It may be constructed, for example, from materials which comprise a metal, a mixture of different metals, a metal alloy, a metal oxide or a mixture of different metal oxides. Alternatively, the anode may be a conductive polymer. Suitable metals comprise the metals of groups Ib, IVb, Va and VIa of the Periodic Table of the Elements, and the transition metals of group VIIIa. When the anode is to be transparent, generally mixed metal oxides of groups IIb, IIIb and IVb of the Periodic Table of the Elements (old IUPAC version) are used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed.

Suitable hole transport materials for layer (2) of the inventive OLED are disclosed, for example, in Kirk-Othmer Encyclopedia of Chemical Technology, 4th edition, vol. 18, pages 837 to 860, 1996. Both hole-transporting molecules and polymers can be used as hole transport material. Customarily used hole-transporting molecules are selected from the group consisting of tris[N-(1-naphthyl)-N-(phenylamino)]triphenylamine (1-NaphDATA), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino) benzaldehyde diphenyl hydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4"-tris(N,N-diphenylamino) tri-phenylamine (TDTA), porphyrin compounds and phthalocyanines such as copper phthalocyanines. Customarily used hole-transporting polymers are selected from the group consisting of polyvinylcarbazoles, (phenylmethyl)polysilanes and polyanilines. It is like possible to obtain hole-transporting polymers by doping hole-transporting molecules into polymers such as polystyrene and polycarbonate. Suitable hole-transporting molecules are the molecules already mentioned above.

In addition, the carbene complexes mentioned above as emitter materials may also be used as hole transport materials, in which case the band gap of the at least one hole transport material is generally greater than the band gap of the emitter material used. In the context of the present application, band gap is understood to mean the triplet energy.

Suitable electron transport materials for layer (4) of the inventive OLEDs comprise metals chelated with oxinoid compounds, such as 2,2',2"-(1,3,5-phenylene)tris[1-phenyl-1H-benzimidazole] (TPBI), tris(8-quinolinolato)aluminum ($Alq_3$), compounds based on phenanthroline, such as 2,9-dimethyl-4,7-diphenyl-1,10-phenanthroline (DDPA=BCP) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). The layer (4) may serve either to facilitate electron transport or as a buffer layer or as a barrier layer in order to prevent quenching of the exciton at the interfaces of the layers of the OLED. The layer (4) preferably improves the mobility of the electrons and reduces quenching of the exciton.

Among the materials mentioned above as hole transport materials and electron transport materials, some may fulfill several functions. For example, some of the electron-conducting materials are simultaneously hole-blocking materials when they have a low-lying HOMO.

As already mentioned above, the inventive compounds of the formula (I) may likewise be used as charge transport or blocker materials, preferably as blocker materials.

The charge transport layers may also be electronically doped in order to improve the transport properties of the materials used, in order firstly to make the layer thicknesses more generous (avoidance of pinholes/short circuits) and in order secondly to minimize the operating voltage of the device. For example, the hole transport materials may be doped with electron acceptors; for example, it is possible to dope phthalocyanines or arylamines such as TPD or TDTA with tetrafluorotetracyanquinodimethane (F4-TCNQ). The electron transport materials may, for example, be doped with alkali metals, for example $Alq_3$ with lithium. Electronic doping is known to those skilled in the art and is disclosed, for example, in W. Gao, A. Kahn, J. Appl. Phys., Vol. 94, No. 1, Jul. 1, 2003 (p-doped organic layers); A. G. Werner, F. Li, K. Harada, M. Pfeiffer, T. Fritz, K. Leo. Appl. Phys. Lett., Vol. 82, No. 25, Jun. 23, 2003 and Pfeiffer et al., Organic Electronics 2003, 4, 89-103.

The cathode (5) is an electrode which serves to introduce electrons or negative charge carriers. Suitable materials for the cathode are selected from the group consisting of alkali metals of group Ia, for example Li, Cs, alkaline earth metals of group IIa, for example calcium, barium or magnesium, metals of group IIb of the Periodic Table of the Elements (old IUPAC version), comprising the lanthanides and actinides, for example samarium. In addition, it is also possible to use metals such as aluminum or indium, and combinations of all metals mentioned. In addition, lithium-comprising organometallic compounds or LiF may be applied between the organic layer and the cathode in order to reduce the operating voltage.

The OLED according to the present invention may additionally comprise further layers which are known to those skilled in the art. For example, between the layer (2) and the light-emitting layer (3) may be applied a layer which facilitates the transport of the positive charge and/or matches the band gap of the layers to one another. Alternatively, this further layer may serve as a protective layer. In an analogous manner, additional layers may be present between the light-emitting layer (3) and the layer (4) in order to facilitate the transport of the negative charge and/or to match the band gap between the layers to one another. Alternatively, this layer may serve as a protective layer.

In a preferred embodiment, the inventive OLED comprises, in addition to layers (1) to (5), at least one of the further layers specified below:
  a hole injection layer between the anode (1) and the hole-transporting layer (2);
  a blocking layer for electrons between the hole-transporting layer (2) and the light-emitting layer (3);
  a blocking layer for holes between the light-emitting layer (3) and the electron-transporting layer (4);
  an electron injection layer between the electron-transporting layer (4) and the cathode (5).

The inventive compounds of the formula (I) may, depending on their substitution pattern, be used as blocker material in the blocking layer for electrons or in the blocking layer for holes as a blocker material.

However, it is also possible that the OLED does not have all of the layers (1) to (5) mentioned; for example, an OLED comprising layers (1) (anode), (3) (light-emitting layer) and (5) (cathode) is likewise suitable, the functions of layers (2) (hole-transporting layer) and (4) (electron-transporting layer) being assumed by the adjacent layers. OLEDs which have layers (1), (2), (3) and (5) or layers (1), (3), (4) and (5) are likewise suitable.

Those skilled in the art are aware of how suitable materials have to be selected (for example on the basis of electrochemical studies). Suitable materials for the individual layers are known to those skilled in the art and are disclosed, for example, in WO 00/70655.

In addition, each of the layers of the inventive OLED mentioned may be formed from two or more layers. In addition, it is possible that some or all of layers (1), (2), (3), (4) and (5) are surface-treated in order to increase the efficiency of charge carrier transport. The selection of the materials for each of the layers mentioned is preferably determined so as to obtain an OLED with high efficiency and lifetime.

The inventive OLED can be produced by methods known to those skilled in the art. In general, the inventive OLED is produced by successive vapor deposition of the individual layers onto a suitable substrate. Suitable substrates are, for example, glass or polymer films. For the vapor deposition, it is possible to use customary techniques such as thermal evaporation, chemical vapor deposition and others. In an alternative process, the organic layers may be coated from solutions or dispersions in suitable solvents, for which coating techniques known to those skilled in the art are employed.

In general, the different layers have the following thicknesses: anode (1) from 500 to 5000 Å, preferably from 1000 to 2000 Å; hole-transporting layer (2) from 50 to 1000 Å, preferably from 200 to 800 Å, light-emitting layer (3) from 10 to 1000 Å, preferably from 100 to 800 Å, electron-transporting layer (4) from 50 to 1000 Å, preferably from 200 to 800 Å, cathode (5) from 200 to 10 000 Å, preferably from 300 to 5000 Å. The position of the recombination zone of holes and electrons in the inventive OLED and hence the emission spectrum of the OLED can be influenced by the relative thickness of each layer. This means that the thickness of the electron transport layer should preferably be selected such that the electron/hole recombination zone lies in the light-emitting layer. The ratio of the layer thicknesses of the individual layers in the OLED depends on the materials used. The layer thicknesses of any additional layers used are known to those skilled in the art.

By virtue of use of the inventive compounds of the formula I as matrix materials in the light-emitting layer of the inventive OLEDs, it is possible to obtain OLEDs with high efficiency. The efficiency of the inventive OLEDs can additionally be improved by optimizing the other layers. For example, it is possible to use high-efficiency cathodes such as Ca or Ba, if appropriate in combination with an intermediate layer of LiF. Shaped substrates and novel hole-transporting materials which bring about a reduction in the operating voltage or an increase in the quantum efficiency can likewise be used in the inventive OLEDs. Furthermore, additional layers may be present in the OLEDs in order to adjust the energy level of the different layers and in order to facilitate electroluminescence.

The inventive OLEDs may be used in all devices in which electroluminescence is useful. Suitable devices are preferably selected from stationary and mobile visual display units and illumination units. Stationary visual display units are, for example, visual display units of computers, televisions, visual display units in printers, kitchen appliances, and advertising panels, illuminations and information panels. Mobile visual display units are, for example, visual display units in cellphones, laptops, digital cameras, vehicles, and destination displays on buses and trains.

In addition, the inventive compounds of the formula I may be used in OLEDs with inverse structure. Preference is given to using the compounds of the formula I used in accordance with the invention in these inverse OLEDs again as matrix materials in the light-emitting layer. The construction of inverse OLEDs and the materials used customarily therein are known to those skilled in the art.

The examples which follow provide additional illustration of the invention.

EXAMPLES

A: Preparation of Inventive Compounds of the Formula (I)

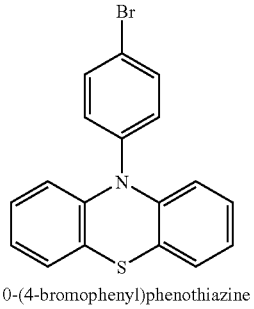

10-(4-bromophenyl)phenothiazine

Phenothiazine (31.4 g, 157 mmol), 1-bromo-4-iodobenzene (50.0 g, 173 mmol), potassium carbonate (32.9 g, 238 mmol) and copper powder (2.0 g, 31 mmol) were heated to 170° C. and stirred at this temperature for 7 h. The reaction melt was cooled to 130° C., admixed with ethyl acetate (80 ml) and stirred under reflux for 30 min. The suspension obtained was transferred to a Soxhlet extractor and extracted under reflux for 16 h. The extraction solution was cooled to room temperature with stirring. Three quarters of the solvent were distilled off, and the product of value was precipitated with ethanol (30 ml) and filtered. 26.7 g (48% of theory) of colorless crystals having a melting point of 132-137° C. were obtained.

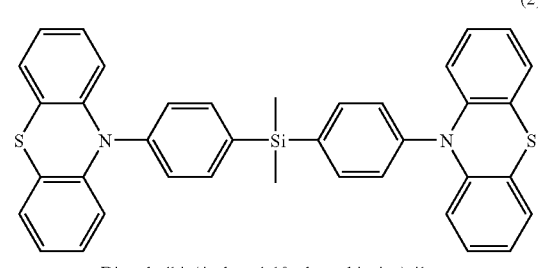

Dimethylbis(4-phenyl-10-phenothiazine)silane

To a mixture of magnesium (0.56 g, 22.6 mmol) and dry THF (6 ml) was added a solution of 10-(4-bromophenyl) phenothiazine (8.0 g, 22.6 mmol) in dry THF (24 ml). After reflux for 2 h, SiMe$_2$Cl$_2$ (1.46 g, 11.3 mmol) was added. After reflux for 2 h, the solution was cooled, filtered and admixed with ice and diethyl ether. The organic phase was removed and concentrated. The residue was crystallized from DMF. 3.00 g (44% of theory) of colorless crystals pure according to elemental analysis were obtained.

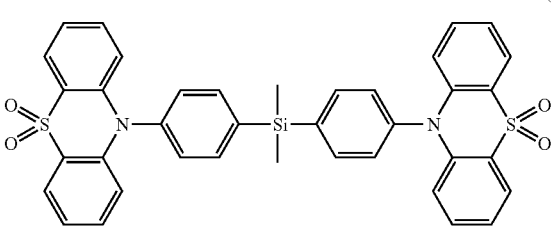

Dimethylbis(4-phenyl-10-phenothiazine S,S-dioxide)silane

Dimethylbis(4-phenyl-10-phenothiazine)silane (2.97 g, 4.90 mmol) were dissolved in methylene chloride (280 ml). After stirring at room temperature for 15 min, 77% m-chloroperbenzoic acid (5.80 g, 23.4 mmol) was added in portions. The reaction solution was stirred at room temperature for 24 h. The organic phase was washed with 10% sodium hydroxide solution (50 ml), 5% hydrochloric acid (50 ml) and with saturated sodium hydrogen carbonate solution (50 ml), and concentrated. The residue was crystallized from DMF. 2.8 g (85% of theory) of colorless crystals having a melting point of 293-298° C. were obtained.

(4)

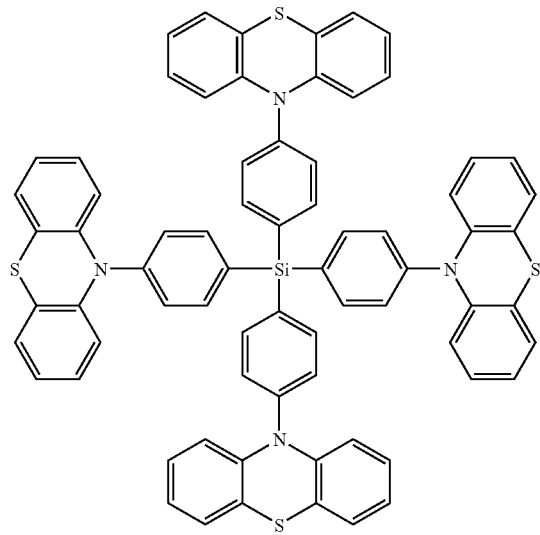

Tetrakis(4-phenyl-10-phenothiazine)silane

To a solution of 10-(4-bromophenyl)phenothiazine (8.0 g, 22.6 mmol) in dry THF (120 ml) was added, at −78° C., nBuLi (14.8 ml, 1.6 M in hexane). After stirring for 1 h, SiMe$_2$Cl$_2$ (0.93 g, 5.4 mmol) in dry THF (12 ml) was added. After 2 h at −78° C., the solution was warmed to room temperature and stirred overnight. The precipitate was filtered and the residue was washed with saturated ammonium chloride solution and demineralized water. The residue was recrystallized from DMF. 3.44 g (57% of theory) of the target product were obtained.

(5)

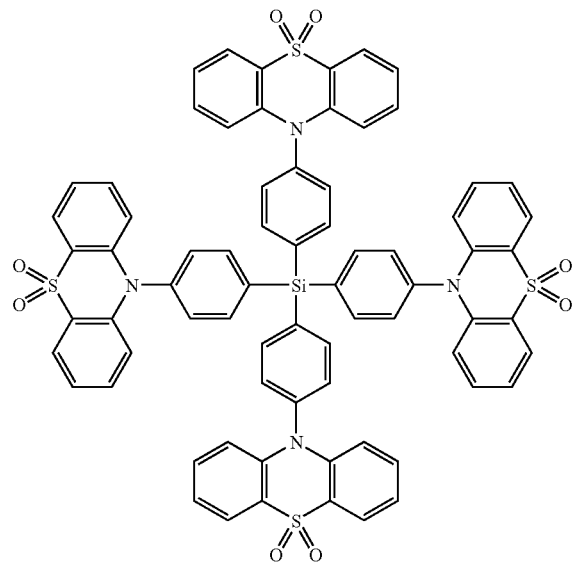

Tetrakis(4-phenyl-10-phenothiazine S,S-dioxide)silane

Tetrakis(4-phenylphenothiazine)silane (3.47 g, 3.08 mmol) were suspended in methylene chloride (1500 ml). After stirring at room temperature for 15 min, 77% m-chloroperbenzoic acid (7.30 g, 29.6 mmol) was added in portions. The resulting solution was stirred at room temperature for 20 h. The organic phase was washed with 10% sodium hydroxide solution (3×30 ml), 5% hydrochloric acid (30 ml) and with saturated sodium hydrogen carbonate solution (30 ml), and concentrated. The residue was crystallized from methylene chloride/acetone. 1.74 g (45% of theory) of colorless crystals were obtained.

(6)

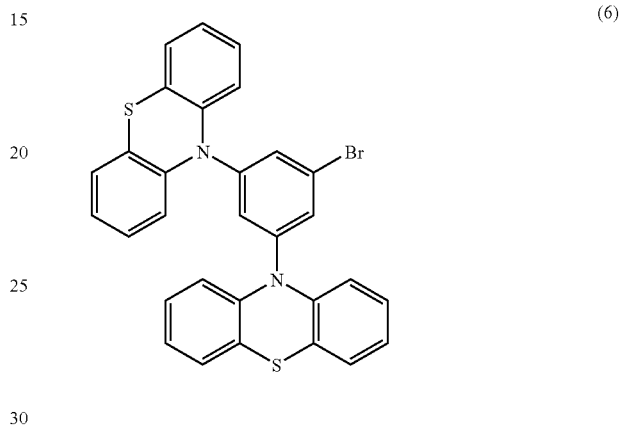

Sodium hydride (60% dispersion in paraffin oil) (28.0 g, 700.0 mmol) was mixed with dry DMF (700 ml) under N$_2$. With stirring, phenothiazine (140.7 g, 700.0 mmol) is added within 10 min. After the evolution of hydrogen had ended (20 min), 1-bromo-3,5-difluorobenzene (68.95 g, 350.0 mmol) in DMF (70 ml) was added within 15 min. The mixture was stirred at 100° C. for 18 h. Sodium hydride (60% dispersion in paraffin oil) was added (4.0 g, 100.0 mmol) and the mixture was stirred at 100° C. for a further 5 h. Sodium hydride (60% dispersion in paraffin oil) was added (4.0 g, 100.0 mmol) and the mixture was stirred at 100° C. for a further 18 h. The mixture was cooled to room temperature, filtered and washed with DMF. The residue was admixed with cyclohexane/ethyl acetate (5:2, 500 ml) and filtered off. 38.9 g (20% of theory) of light yellow solid (6) were obtained.

(7)

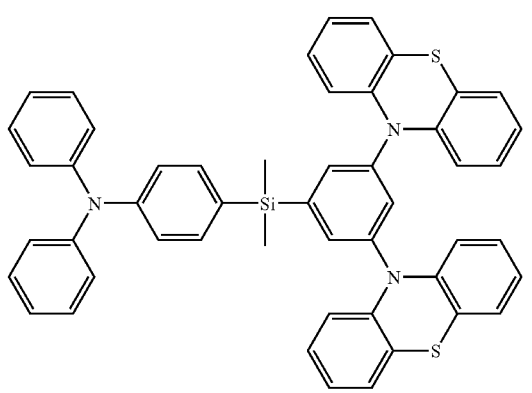

To a solution of (4-bromophenyl)diphenylamine (8.40 g, 25.20 mmol) in dry THF (105 ml), at −78° C., was added dropwise nBuLi (16.8 ml, 26.6 mmol, 1.6 M in hexane). After stirring at −78° C. for 60 min, this solution was added dropwise to a solution of dichlorodimethylsilane (3.47 g, 26.6 mmol) in THF (140 ml) at −78° C. The reaction mixture was warmed to 0° C. within 40 min and stirred at 0° C. for 1 h. The mixture was cooled again to −78° C., and a solution of lithium 3,5-bis(10-phenothiazine)-1-phenoxide (from (6) (14.0 g, 25.2 mmol) and nBuLi (16.8 ml, 26.6 mmol, 1,6 M in hexane)) in THF (105 ml) was added. After stirring at −78° C. for 1 h, the mixture was warmed to room temperature and stirred overnight. The mixture was admixed with saturated ammonium chloride solution (70 ml) and filtered. The organic phase was washed with water and dried (Na$_2$SO$_4$). After column chromatography (SiO$_2$, 40:1 hexane/ethyl acetate) and recrystallization from ethyl acetate, 2.88 g (14% of theory) of the target product (7) were obtained.

(8)

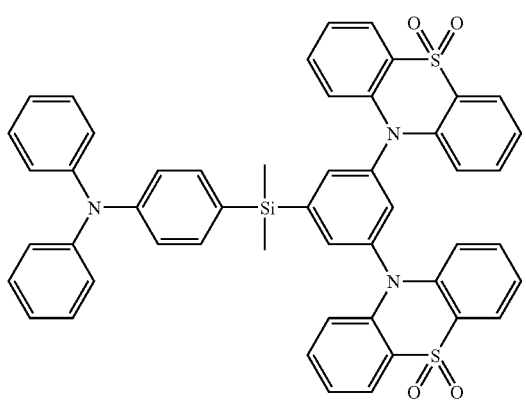

(7) (2.8 g, 3.6 mmol) was dissolved in methylene chloride (100 ml). After stirring at room temperature for 15 min, 77% m-chloroperbenzoic acid (3.55 g, 14.4 mmol) in methylene chloride (40 ml) was slowly added dropwise at 0-5° C. The resulting solution was stirred at 0-5° C. for 20 h. The organic phase was washed with 10% sodium hydroxide solution (3×20 ml), 5% hydrochloric acid (30 ml) and with saturated sodium hydrogencarbonate solution (3×20 ml), dried (Na$_2$SO$_4$) and concentrated. After column chromatography (SiO$_2$, CH$_2$Cl$_2$), 1.1 g (38% of theory) of the target product (8) were obtained.

B: Use Example: Production of an OLED

B1: Use of the Compound (3) as a Matrix Material

The ITO substrate used as the anode is cleaned first with commercial detergents for LCD production (Deconex® 20NS and neutralizing agent 25ORGAN-ACID®) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO.

Thereafter, the organic materials specified below are applied to the cleaned substrate by vapor deposition at a rate of approx. 0.5-5 nm/min at about 10$^{-9}$ mbar. The hole conductor and exciton blocker applied to the substrate is Ir(dpbic)$_3$ (V1) with a thickness of 20 nm.

(V1)

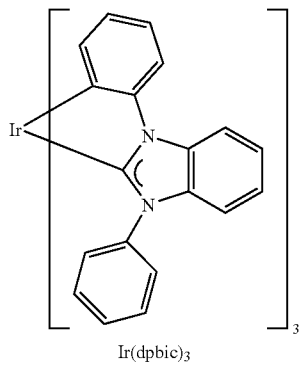

Ir(dpbic)$_3$ (For preparation, see Ir complex (7) in application WO 2005/019373 A2.)

Subsequently, a mixture of 16% by weight of the compound CN-PMBIC (V2):

(V2)

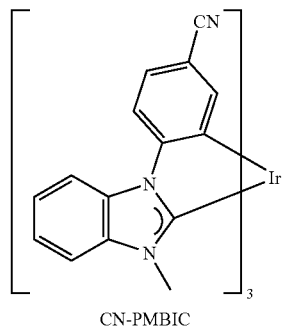

CN-PMBIC (For preparation see example 3 in WO 2006/056418 A2.)
and 84% by weight of the compound dimethylbis(4-phenylphenothiazine S,S-dioxide)silane (3) are applied by vapor deposition in a thickness of 20 nm, the first compound functioning as an emitter, the latter as a matrix material.

Subsequently, the material mPTO2 (1,3-phenylene-10,10'-bis(phenothiazine) 5,5'-dioxide (V3)) is applied by vapor deposition with a thickness of 10 nm as an exciton and hole blocker.

(V3)

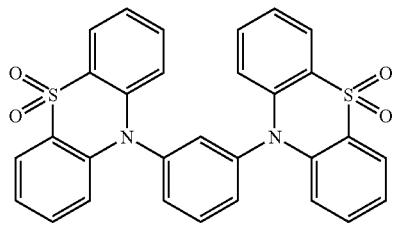

Next, an electron transport material TPBI (1,3,5-tris(N-phenylbenzylimidazol-2-yl)benzene) is applied by vapor deposition in a thickness of 65 nm, as are a 0.75 nm-thick lithium fluoride layer and finally a 110 nm-thick Al electrode.

To characterize the OLED, electroluminescence spectra are recorded at various currents and voltages. In addition, the current-voltage characteristic is measured in combination with the emitted light output. The light output can be converted to photometric parameters by calibration with a photometer.

For the OLED described, the following electrooptical data are obtained:

| | |
|---|---|
| Emission maximum | 455 nm |
| CIE(x, y) | 0.17; 0.13 |
| Photometric efficiency at 3 V | 6.0 cd/A |
| Power efficiency at 3 V | 6.3 lm/W |
| External quantum yield at 3 V | 5.4% |
| Luminance at 10 V | 400 cd/m² |

B2: Use of the Compound (3) as an Exciton and Hole Blocker

The ITO substrate used as the anode is cleaned first with commercial detergents for LCD production (Deconex® 20NS and neutralizing agent 25ORGAN-ACID®) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO.

Thereafter, the organic materials specified below are applied to the cleaned substrate by vapor deposition at a rate of approx. 0.5-5 nm/min at about $10^{-9}$ mbar. The hole conductor and exciton blocker applied to the substrate is Ir(dpbic)$_3$ (V1) with a thickness of 30 nm.

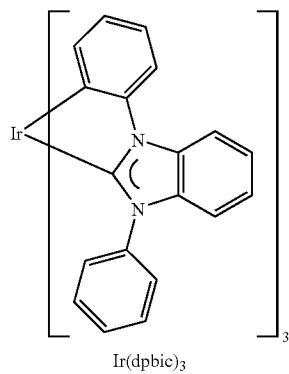

Ir(dpbic)$_3$ (For preparation, see Ir complex (7) in application WO 2005/019373 A2.)

Subsequently, a mixture of 30% by weight of the compound CN-PMBIC

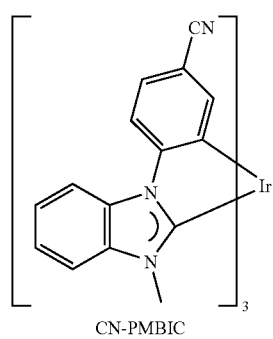

CN-PMBIC (For preparation see example 3 in WO 2006/056418 A2.) and 70% by weight of compound (V4) are applied by vapor deposition in a thickness of 20 nm, the first compound functioning as an emitter, the latter as a matrix material.

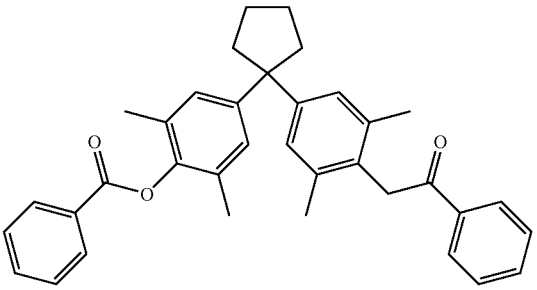

Subsequently, compound (3) is applied by vapor deposition with a thickness of 10 nm as an exciton and hole blocker.

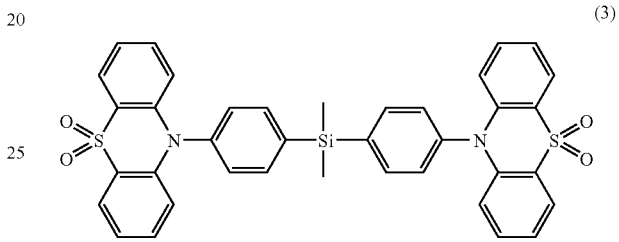

Next, an electron transport material TPBI (1,3,5-tris(N-phenylbenzylimidazol-2-yl)benzene) is applied by vapor deposition in a thickness of 40 nm, as are a 0.75 nm-thick lithium fluoride layer and finally a 110 nm-thick Al electrode.

To characterize the OLED, electroluminescence spectra are recorded at various currents and voltages. In addition, the current-voltage characteristic is measured in combination with the emitted light output. The light output can be converted to photometric parameters by calibration with a photometer.

For the OLED described, the following electrooptical data are obtained:

| | |
|---|---|
| Emission maximum Blocker | 455 nm |
| CIE(x, y) | 0.16; 0.12 |
| Photometric efficiency at 4.5 V | 8.8 cd/A |
| Power efficiency at 4.5 V | 6.1 lm/W |
| External quantum yield at 4.5 V | 8.8% |

C: Process for Preparing Selected Carbene Complexes

Ir(DBF-MIC)$_3$ (V5)

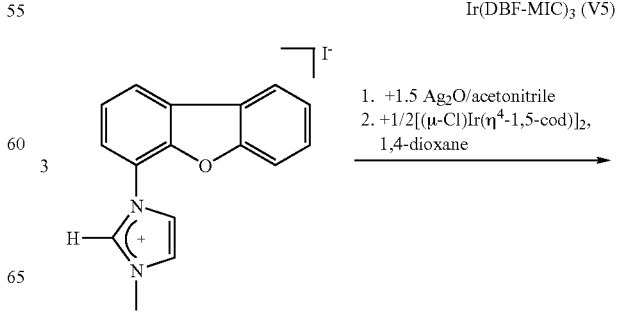

1. +1.5 Ag$_2$O/acetonitrile
2. +1/2[(μ-Cl)Ir(η$^4$-1,5-cod)]$_2$, 1,4-dioxane

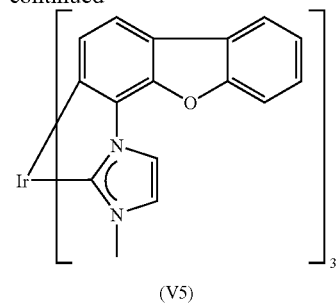

(V5)

3.48 g (9.2 mmol) of imidazolium iodide and 1.07 g (4.6 mmol) of silver oxide are suspended in 60 ml of acetonitrile and stirred at room temperature overnight. Subsequently, the suspension is concentrated to dryness, taken up with 100 ml of 1,4-dioxane and metered into a solution of 0.62 g (0.92 mmol) of [(μ-Cl)(η$^4$-1,5-cod)Ir]$_2$ and 60 ml of 1,4-dioxane within a half hour. Thereafter, the mixture is stirred at room temperature for 1 hour, at 70° C. for 2 hours and under reflux for 18 hours. After cooling, the reaction mixture is concentrated to dryness and extracted with dichloromethane, and the extract is subjected to a column chromatography purification (eluent: 1. 2:1 methylene chloride:cyclohexane to isolate the isomer mixture and 2. 1:1 ethyl acetate: cyclohexane to separate the isomers, ratio of the isomers in the reaction mixture: mer|fac approx. 3/1). This affords approx. 0.61 g (35%) of mer-isomer and 0.1 g (6%) of fac-isomer as a light yellow powder.

Meridional Isomer:

$^1$H NMR: (DMSO, 500 MHz): 8.40 (d, J=2.0 Hz, 1H, CH), 8.34 (d, J=2.1 Hz, 1H, CH), 8.22 (d, J=2.1 Hz, 1H, CH), 7.90-7.85 (m, 1H, CH), 7.69-7.65 (m, 1H, CH), 7.43-7.13 (m, 16H, CH), 6.75 (d, $^3J_{H,H}$=7.5 Hz, 1H, CH), 6.68 (d, $^3J_{H,H}$=7.7 Hz, 1H, CH), 6.56 (d, $^3J_{H,H}$=7.6 Hz, 1H, CH), 3.13 (s, 3H, CH$_3$), 3.05 (s, 3H, CH$_3$), 2.99 (s, 3H, CH$_3$).

Facial Isomer:

$^1$H NMR: (DMSO, 500 MHz): 8.28 (d, J=1.95 Hz, 3H, CH), 7.88-7.89 (m, 3H, CH), 7.67-7.68 (m, 3H, CH), 7.43-7.12 (m, 12H, CH), 6.50 (d, $J_{H,H}$=7.5 Hz, 3H, CH), 3.14 (s, 9H, CH$_3$).

[(PMIC)$_2$IrCl]$_2$ (V6)

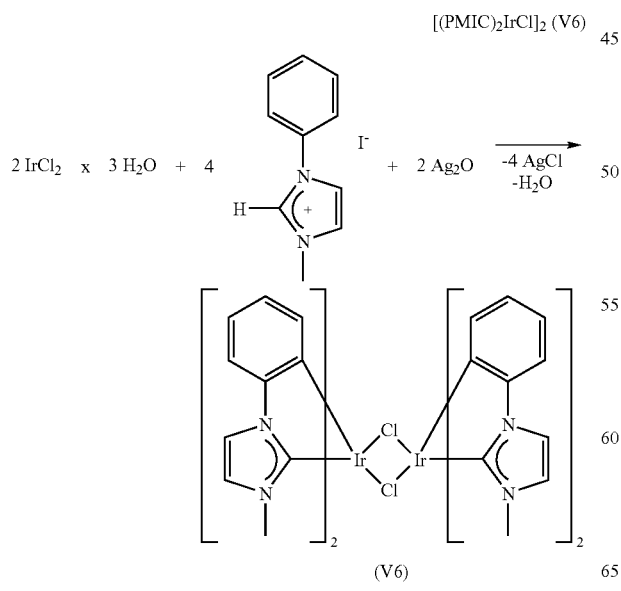

(V6)

4.29 g (18.5 mmol) of silver oxide, 9.47 g (33.1 mmol) of imidazolium iodide and 3.56 g (10.1 mmol) of iridium trichloride trihydrate are suspended in 350 ml of 2-ethoxyethanol and stirred in the dark at 120° C. for 15 h. Thereafter, the solvent is removed under reduced pressure and the residue is extracted with methylene chloride. The extract is concentrated to about a quarter of its volume and admixed with methanol. The solid which precipitates out is filtered off and dried. 1.7 g of [(PMIC)$_2$IrCl]$_2$ are obtained (31%).

$^1$H NMR: (CD$_2$Cl$_2$, 500 MHz): δ=7.59 (d, J=2.3 Hz, 4H, CH), 7.17 (d, J=1.7 Hz, 4H, CH), 6.99 (d, $^3J_{H,H}$=7.2 Hz, 4H, CH), 6.73 (pt, $^3J_{H,H}$=7.5 Hz, 4H, CH), 6.45 (pt, $^3J_{H,H}$=7.9 Hz, 4H, CH), 6.09 (d, $^3J_{H,H}$=7.3 Hz, 4H, CH), 3.91 (s, 12H, CH$_3$).

(PMIC)$_2$Irpic (V7)

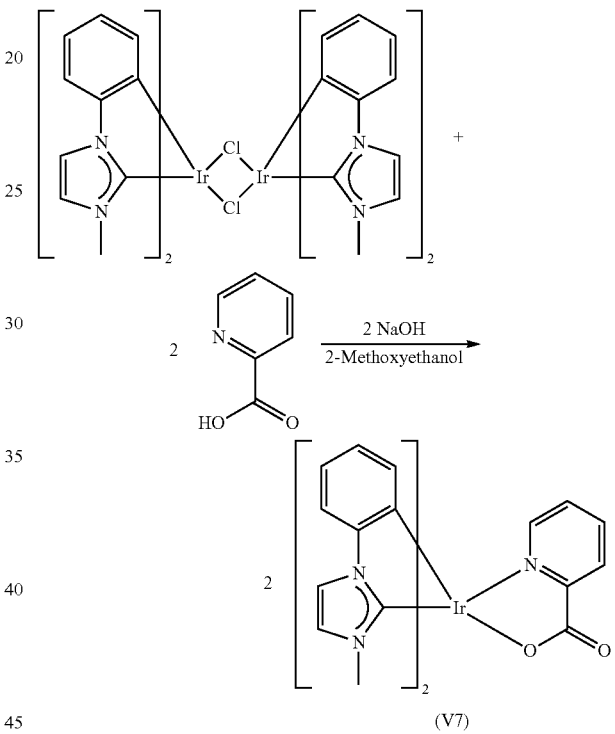

(V7)

A solution of 0.41 g (3.32 mmol) of picolinic acid in methoxyethanol (30 ml) is admixed with 3.32 ml of sodium hydroxide solution (1M, 3.32 mmol) within 10 min and stirred at room temperature for 15 min. Thereafter, the reaction mixture is added within 10 min to a suspension of 0.9 g (0.83 mmol) of [(PMIC)$_2$IrCl]$_2$ in methoxyethanol (80 ml). The mixture is stirred at room temperature for 15 min and then heated at reflux for 21 h. After cooling, the reaction mixture is admixed with water (300 ml). The precipitate which forms is filtered off, dried and subjected to column chromatography purification (eluent: ethyl acetate/methanol=1/0.25). 0.64 g of (PMIC)$_2$IrPic is obtained (61%).

$^1$H NMR: (CD$_2$Cl$_2$, 500 MHz): δ=3.00 (s, 3H, CH$_3$), 3.86 (s, 3H, CH$_3$), 6.31-6.33 (m, 1H, CH), 6.42-6.44 (m, 1H, CH), 6.59-6.63 (m, 2H, CH), 6.83-6.88 (m, 2H, CH), 6.90-6.91 (m, 1H, CH), 6.98-6.99 (m, 1H, CH), 7.08 (d, J=7.8 Hz, 2H, CH), 7.21-7.24 (m, 1H, CH), 7.46-7.47 (m, 2H, CH), 7.80-7.83 (dt, J=7.7 Hz, J=1.5 Hz, 1H, CH), 7.92-7.93 (m, 1H, CH), 8.13-8.15 (m, 1H, CH).

(PMIC)₂IrPicOMe (V8)

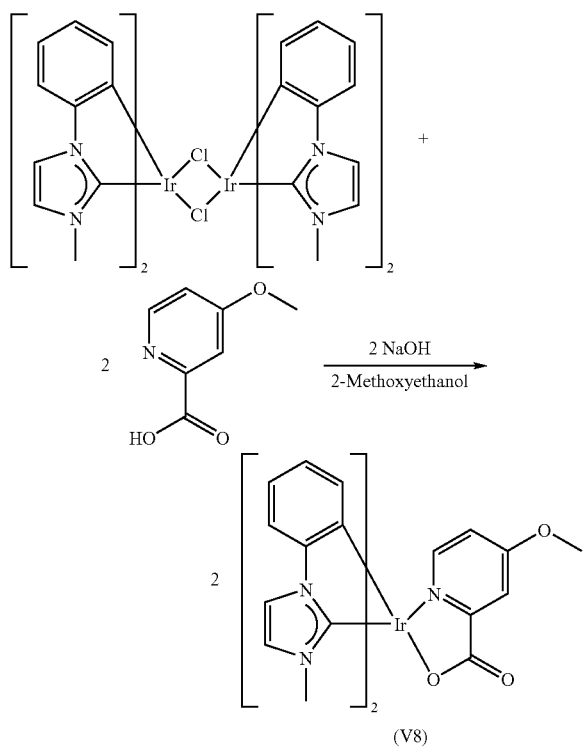

(V8)

A suspension of 0.68 g (4.44 mmol) of 4-methoxypicolinic acid in 70 ml of 2-methoxyethanol is admixed within 10 min with 4.44 ml of sodium hydroxide solution (1M, 4.44 mmol). The mixture is stirred at room temperature for 15 min, before the mixture is added slowly to a suspension of 1.2 g (1.11 mmol) of [(PMIC)₂IrCl]₂ and 80 ml of 2-methoxyethanol. The mixture is stirred at room temperature for 15 min and then heated at reflux for 21 h. After cooling, the reaction mixture is admixed with water (600 ml). The precipitate which forms is filtered off, dried and purified by column chromatography (eluent: ethyl acetate/methanol=1/0.25). 0.93 g of PMIC₂IrPicOMe is obtained (64%).

$^1$H NMR: (CD₂Cl₂, 500 MHz): δ=3.07 (s, 3H, CH₃), 3.85 (s, 3H, CH₃), 3.91 (s, 3H, CH₃), 6.33 (dd, J=7.3 Hz, J=1.4 Hz, 1H, CH), 6.42 (dd, J=7.4 Hz, J=1.4 Hz, 1H, CH), 6.57-6.61 (m, 2H, CH), 6.74 (dd, J=6.3 Hz, J=2.9 Hz, 1H, CH), 6.81-6.86 (m, 2H, CH), 6.92 (d, J=2.1 Hz, 1H, CH), 6.98 (d, J=2.1 Hz, 1H, CH), 7.07 (dd, J=4.8 Hz, J=1.3 Hz, 1H, CH), 7.08 (dd, J=4.6 Hz, J=1.3 Hz, 1H, CH), 7.46 (dd, J=4.1 Hz, J=2.1 Hz, 2H, CH), 7.65 (d, J=6.2 Hz, 1H, CH), 7.72 (d, J=2.5 Hz, 1H, CH).

(PMIC)₂Ir(acac-F₆) (V9)

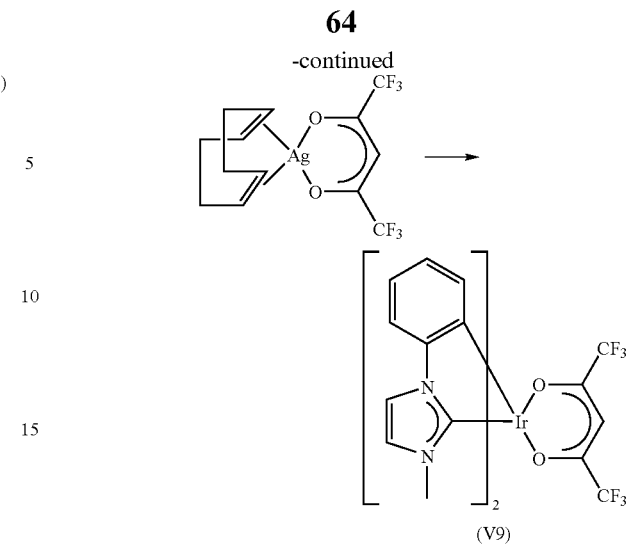

(V9)

A solution of 0.22 g (0.2 mmol) [(PMIC)₂IrCl]₂ in 60 ml of methylene chloride was admixed with a solution of 0.17 g (0.4 mmol) of (cod)Ag(acac-F₆) in 30 ml of methylene chloride. The mixture was stirred under reflux for 2 h and at room temperature for 18 h. The solvent was then removed under reduced pressure and the residue was purified by column chromatography (eluent: CH₂Cl₂). 0.28 g (96%) of red powder is obtained.

$^1$H NMR: (CD₂Cl₂, 500 MHz): δ=7.50 (s, 2H), 7.11 (s, 2H), 7.03 (m, 2H), 6.81 (m, 2H), 6.56 (m, 2H), 6.19 (m, 2H), 5.98 (s, 1H), 3.79 (s, 6H).

mer-tris-[1-(4'-phenylsulfonylphenyl)-3-methylbenz-imidazol-2-ylidene-C2,C2']-iridium(III)(V10)

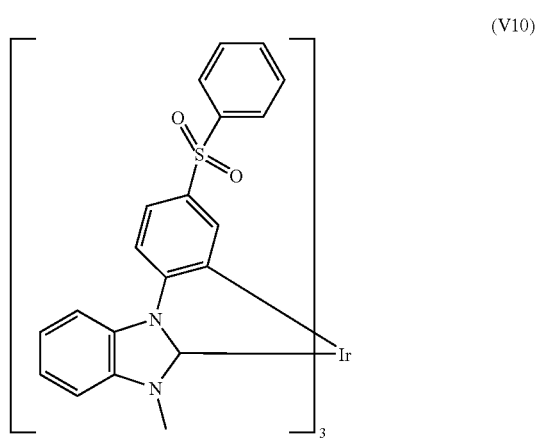

1-(4'-phenylsulfonylphenyl)-benzimidazole

To a solution of benzimidazole (11.8 g, 0.10 mol) in DMF (500 ml) is added, at room temperature under nitrogen, sodium hydride (60% in mineral oil, 4.4 g, 0.11 mol), and the mixture is stirred for 10 min. The mixture is admixed with 4-chlorophenyl phenylsulfone (26.1 g, 0.10 mol) and stirred at 100° C. for 16 h. After again adding sodium hydride (60% in mineral oil, 2.0 g, 0.05 mol) at room temperature, the mixture is stirred at 130° C. for 16 h. After cooling to room temperature, the mixture is added to ice-water. Precipitated product is filtered off and washed with water. Yield: 91%.

$^1$H NMR (d$_6$-DMSO, 400 MHz): δ=7.35 (m$_c$, 2H), 7.64-7.82 (m, 5H), 7.98 (d, 2H), 8.06 (d, 2H), 8.20 (d, 2H), 8.67 (s, 1H).

1-(4'-phenylsulfonylphenyl)-3-methylbenzimidazolium tetrafluoroborate

A solution of 1-(4'-phenylsulfonylphenyl)benzimidazole (6.7 g, 20 mmol) in dichloromethane (100 ml) is admixed at −10° C. with trimethyloxonium tetrafluoroborate (3.3 g, 22 mmol) and stirred under argon for 16 h. After adding ethanol, the precipitate which forms is filtered off and washed with cold petroleum ether. Yield: 80%.

$^1$H NMR (d$_6$-DMSO, 400 MHz): δ=4.17 (s, 3H), 7.67-7.83 (m, 5H), 7.94 (d, 1H), 8.04-8.12 (m, 4H), 8.15 (d, 1H), 8.36 (d, 2H), 10.14 (s, 1H).

mer-tris-[1-(4'-phenylsulfonylphenyl)-3-methylbenzimidazol-2-ylidene-C2,C2']-iridium(III)(VII)

A suspension of 1-(4'-phenylsulfonylphenyl)-3-methylbenzimidazolium tetrafluoroborate (4.4 g, 10 mmol) in dioxane (100 ml) is admixed under argon at room temperature with KHMDS (0.5 M in toluene, 20 ml, 10 mmol) and stirred for 15 min. After adding 1,5-cyclooctadiene)indium(I) chloride dimer (0.7 g, 1 mmol), the mixture is stirred under reflux for 16 h. After cooling to room temperature, the precipitate is filtered off and washed with methyl tert-butyl ether. The combined filtrates are concentrated to dryness and purified by column chromatography (aluminum oxide, dichloromethane, butanone). Yield: 56%.

$^1$H NMR (d$_6$-DMSO, 400 MHz): δ=2.82 (s, 3H), 2.99 (s, 3H), 3.15 (s, 3H), 6.61 (d, 1H), 6.98 (d, 1H), 7.01 (d, 1H), 7.30-7.72 (m, 27H), 8.09-8.16 (m, 3H), 8.35-8.44 (m, 3H).

Tris-[1-(4'-methoxycarbonylphenyl)-3-methylimidazol-2-ylidene-C2,C2']-iridium(III)

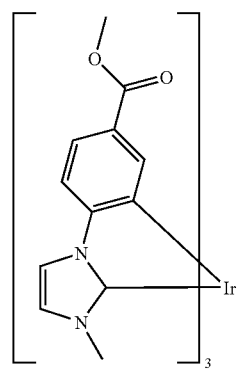

(V11)

1-(4'-methoxycarbonylphenyl)imidazole

A mixture of imidazole (132 g, 1.9 mol), methyl 4-fluorobenzoate (170 ml, 1.3 mol) and potassium carbonate (357 g, 2.6 mol) in DMSO (200 ml) is stirred at 120° C. for 3 h. After cooling to room temperature, the mixture is added to ice-water. Precipitated product is filtered off and washed with water. Yield: 59%.

$^1$H NMR (d$_6$-DMSO, 400 MHz): δ=3.89 (s, 3H), 7.17 (m$_c$, 1H), 7.86 (d, 2H), 7.90 (m$_c$, 1H), 8.08 (d, 2H), 8.44 (m$_c$, 1H).

1-(4'-methoxycarbonylphenyl)-3-methylimidazolium iodide

A solution of 1-(4'-methoxycarbonylphenyl)imidazole (153 g, 0.76 mol) in 1:1 THF/methanol (600 ml) is admixed with methyl iodide (196 ml, 2.27 mol) and stirred under argon at room temperature for 16 h. After concentration of the solution, the precipitated product is filtered off and washed with THF. Yield: 59%.

$^1$H NMR (d$_6$-DMSO, 400 MHz): δ=3.90 (s, 3H), 3.95 (s, 3H), 7.94 (d, 2H), 7.98 (m$_c$, 1H), 8.21 (d, 2H), 8.38 (m$_c$, 1H), 9.89 (s, 1H).

Tris-[1-(4'-methoxycarbonylphenyl)-3-methylimidazol-2-ylidene-C2,C2']-iridium(III)

A suspension of 1-(4'-methoxycarbonylphenyl)-3-methylimidazolium iodide (148.0 g, 431 mmol) and silver(I) oxide (50.4 g, 216 mmol) in dioxane (400 ml) is stirred under argon at room temperature for 16 h. The mixture is admixed with (1,5-cyclooctadiene indium(I) chloride dimer (33.2 g, 43 mmol) and stirred under reflux for 16 h. After cooling to room temperature, the precipitate is filtered off and washed with dichloromethane. The combined filtrates are concentrated to dryness and purified by column chromatography (aluminum oxide, 1:1 ethyl acetate/methanol). Mixed fractions which comprise the product as the mer- and fac-isomer are concentrated to dryness and dissolved in 1:1 acetone/methanol. The solution is admixed with 1 M hydrochloric acid and stirred under reflux for 16 h. The precipitated mer-isomer is filtered off and washed with a little acetone. Yield: 45%.

mer-isomer: $^1$H NMR (d$_6$-DMSO, 400 MHz): δ=2.89 (s, 3H), 2.96 (s, 3H), 2.99 (s, 3H), 3.60 (s, 3H), 3.67 (s, 3H), 3.69 (s, 3H), 7.12 (s, 1H), 7.18 (s, 1H), 7.24 (s, 1H), 7.27 (s, 1H), 7.29 (s, 1H), 7.31 (s, 1H), 7.38-7.49 (m, 6H), 7.98 (s, 1H), 8.04 (s, 1H), 8.06 (s, 1H).

fac-isomer: $^1$H NMR (d$_6$-DMSO, 400 MHz): δ=3.00 (s, 9H), 3.60 (s, 9H), 7.06 (d, 3H), 7.21 (d, 3H), 7.43-7.51 (m, 6H), 7.99 (d, 3H).

Bis[(2-phenyl)-2-pyrazolinato-N,C$^2$)](1-phenyl-3-methylimidazolin-2-ylidene-C,C$^2$) (V12) iridium(III)

Compound (V12) is prepared in analogy to example 3 in US 2005/0260441 A1 with the difference that, instead of [(F2 ppz)$_2$IrCl]$_2$[(ppz)$_2$IrCl]$_2$ is used.

The invention claimed is
1. A compound of the general formula I

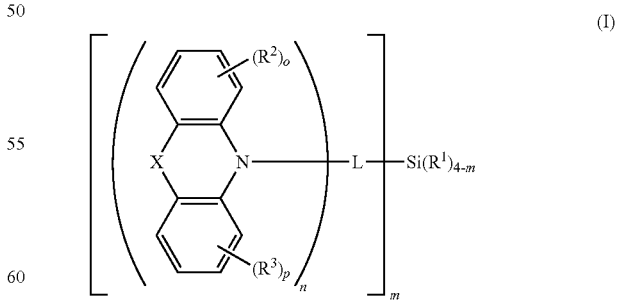

in which
X is SO$_2$ or SO;
R$^1$ is in each case independently optionally substituted aryl, optionally substituted heteroaryl or optionally substituted alkyl;

R², R³ are in each case independently optionally substituted alkyl, optionally substituted aryl, optionally substituted heteroaryl or substituents having donor or acceptor action;
m is 1, 2, 3 or 4;
n is 1 or 2;
o, p are each independently 0, 1, 2, 3 or 4;
L is a bridging group selected from the group consisting of

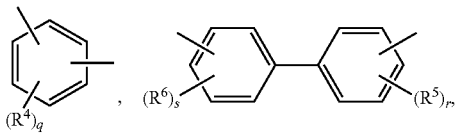

—CH₂—(B)ⱼ— and optionally substituted heteroarylene;
R⁴, R⁵, R⁶ are in each case independently optionally substituted alkyl, optionally substituted aryl, optionally substituted heteroaryl or substituents having donor or acceptor action;
q, r, s are each independently 0, 1, 2, 3 or 4;
B is an alkylene bridge —CₖH₂ₖ—CH₂—, in which one or more nonadjacent CH₂ groups of the —CₖH₂ₖ— unit may be replaced by oxygen or NR⁷;
R⁷ is hydrogen or alkyl;
k is 1, 2, 3, 4, 5, 6, 7 or 8; and
j is 0 or 1.

2. The compound according to claim 1, in which:
X is SO₂;
m is 2, 3 or 4;
o, p are each 0, 1 or 2;
L is

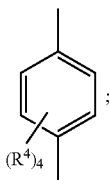

and
q is 0, 1 or 2.

3. The compound according to claim 1, wherein at least two of the L or R¹ radicals or groups bonded to the Si are aromatic radicals or groups.

4. The compound according to claim 1, in which:
L is

and
o, p and q are each 0.

5. An OLED comprising at least one compound according to claim 1.

6. An OLED wherein at least one compound according to claim 1 is used as a matrix material and/or a blocker material.

7. The OLED according to claim 6, wherein the matrix material and/or blocker material is used together with a triplet emitter.

8. A light-emitting layer comprising at least one compound according to claim 1 and at least one triplet emitter.

9. A hole and/or exciton blocker layer comprising at least one compound according to claim 1.

10. A process for preparing compounds according to claim 1, comprising:
(i) preparing a phenothiazine derivate (II)

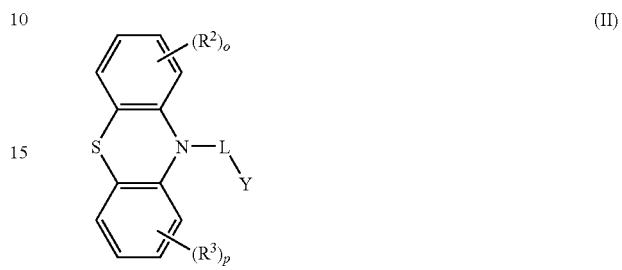

in which
R², R³ are in each case independently optionally substituted alkyl, optionally substituted aryl, optionally substituted heteroaryl or a radical having donor or acceptor action;
o, p are each independently 0, 1, 2, 3 or 4;
L is a bridging group selected from the group consisting of

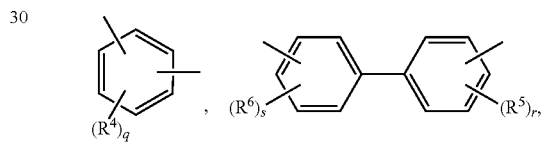

—CH₂—(B)ⱼ— and optionally substituted heteroarylene;
R⁴, R⁵, R⁶ are in each case independently optionally substituted alkyl, optionally substituted aryl, optionally substituted heteroaryl or substituents having donor or acceptor action;
q, r, s are each independently 0, 1, 2, 3 or 4;
B is an alkylene bridge —CₖH₂ₖ—CH₂—, in which one or more nonadjacent CH₂ groups of the —CₖH₂ₖ— unit may be replaced by oxygen or NR⁷;
R⁷ is hydrogen or alkyl;
k is 1, 2, 3, 4, 5, 6, 7 or 8;
j is 0 or 1; and
Y is a halogen selected from the group consisting of F, Cl and Br;
by reacting phenothiazine or a phenothiazine derivate of the formula (III)

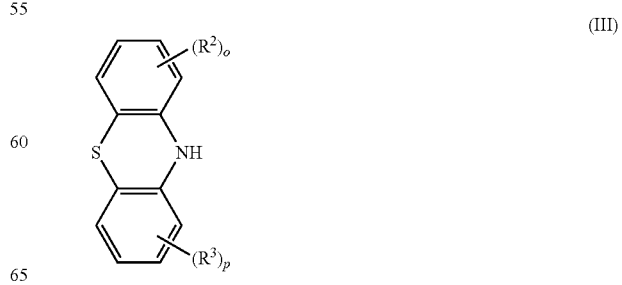

in which R², R³, o and p are each as defined above with a bifunctional compound of the formula (IV)

Z-L-Y  (IV)

in which L and Y are each as defined above and
Z is iodine, fluorine, bromine or tosyl;
(ii) preparing phenothiazine derivates of the formula (V)

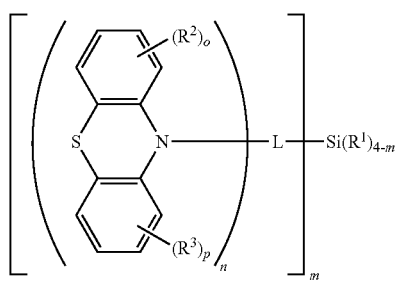

in which the radicals and indices are each as defined above, and
m is 1, 2, 3 or 4, and
n is 1 or 2,
by reacting the phenothiazine derivate (II) with a haloalkyl/arylsilane of the general formula (VIa) or with an alkoxysilane of the general formula (VIb)

$(R^8)_t Si(Hal)_{4-t}$  (VIa)

$(R^8)_t Si(OR^9)_{4-t}$  (VIb)

in which
$R^8$ is optionally substituted aryl, optionally substituted heteroaryl or optionally substituted alkyl;
Hal is a halogen;
t is 1, 2 or 3; and
$R^9$ is alkyl, and
(iii) preparing the phenothiazine S-oxide or S,S-dioxide derivatives of the formula (I)
by reacting the phenothiazine derivates of the formula (V) with an oxidizing agent.

11. The method of using compounds according to claim 1 in OLEDs.

12. Stationary visual display units of computers, televisions, printers, kitchen appliances, advertising panels, illuminations, and information panels and mobile visual display units in cellphones, laptops, digital cameras, and vehicles and destination displays on buses and trains and illumination units, comprising at least one organic light-emitting diode according to claim 5.

* * * * *